US010633435B2

(12) United States Patent
Van Kolen et al.

(10) Patent No.: US 10,633,435 B2
(45) Date of Patent: Apr. 28, 2020

(54) ANTI-PHF-TAU ANTIBODIES AND USES THEREOF

(71) Applicant: JANSSEN PHARMACEUTICA NV, New Brunswick, NJ (US)

(72) Inventors: Kristof Van Kolen, Haacht (BE); Marc Mercken, Turnhout (BE); Linda Barone, Exton, PA (US); Eilyn R. Lacy, Lansdowne, PA (US); Rupesh Nanjunda, Hatfield, PA (US); John Wheeler, Downington, PA (US); Jinquan Luo, Malvern, PA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

(21) Appl. No.: 16/291,303

(22) Filed: Mar. 4, 2019

(65) Prior Publication Data
US 2019/0270793 A1 Sep. 5, 2019

Related U.S. Application Data

(60) Provisional application No. 62/638,535, filed on Mar. 5, 2018.

(51) Int. Cl.
| *C07K 16/18* | (2006.01) |
| *G01N 33/563* | (2006.01) |
| *C12N 15/85* | (2006.01) |
| *A61P 25/28* | (2006.01) |
| *A61P 25/16* | (2006.01) |
| *C12N 15/62* | (2006.01) |

(52) U.S. Cl.
CPC .............. *C07K 16/18* (2013.01); *A61P 25/16* (2018.01); *A61P 25/28* (2018.01); *C12N 15/62* (2013.01); *C12N 15/85* (2013.01); *G01N 33/563* (2013.01); *G01N 2800/2821* (2013.01); *G01N 2800/2835* (2013.01)

(58) Field of Classification Search
None
See application file for complete search history.

(56) References Cited

U.S. PATENT DOCUMENTS

| 4,816,567 A | 3/1989 | Cabilly et al. |
| 5,225,539 A | 7/1993 | Winter |
| 7,657,380 B2 | 2/2010 | Lazar et al. |
| 2010/0021477 A1 | 1/2010 | Tsui et al. |

(Continued)

FOREIGN PATENT DOCUMENTS

| WO | 1992/01047 A1 | 1/1992 |
| WO | 2002/098897 A3 | 12/2002 |

(Continued)

OTHER PUBLICATIONS

Abhinandan, et al., Analysis and improvements to Kabat and Structurally Correct Numbering of antibody Variable domains., Molelcular Immunology, Jul. 9, 2008, pp. 3832-3839, vol. 45.

(Continued)

Primary Examiner — Aurora M Fontainhas

(57) ABSTRACT

Monoclonal anti-tau antibodies and antigen-binding fragments thereof are described. Also described are nucleic acids encoding the antibodies, compositions comprising the antibodies, methods of producing the antibodies and using the antibodies for treating or preventing conditions such as tauopathies. The antibodies of the invention may also be used to quantify tau in biological samples.

19 Claims, 14 Drawing Sheets

Specification includes a Sequence Listing.

| SEQ ID NO | | | PT82 | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| 33 | 103 | 122 | 68 | | | | A | E | E | A | G | I | G | D | T | P | S | L | E | D | E | A | A | G | H | M | | | | | | |
| 34 | 105 | 124 | 2904 | | | | | E | A | G | I | G | D | T | P | S | L | E | D | E | A | A | G | H | M | T | Q | | | | | |
| 35 | 107 | 126 | 2921 | | | | | | G | I | G | D | T | P | S | L | E | D | E | A | A | G | H | M | T | Q | A | R | | | | |
| 36 | 109 | 128 | 2924 | | | | | | | G | D | T | P | S | L | E | D | E | A | A | G | H | M | T | Q | A | R | M | M | | | |
| 37 | 111 | 130 | 2927 | | | | | | | | T | P | S | L | E | D | E | A | A | G | H | M | T | Q | A | R | M | M | S | K | | |
| 38 | 113 | 132 | 2927 | | | | | | | | | S | L | E | D | E | A | A | G | H | M | T | Q | A | R | M | M | S | K | S | K | |
| 39 | 115 | 134 | 2919 | | | | | | | | | | E | D | E | A | A | G | H | M | T | Q | A | R | M | M | S | K | S | K | D | G |
| 40 | 117 | 136 | 2919 | | | | | | | | | | | E | A | A | G | H | M | T | Q | A | R | M | M | S | K | S | K | D | G | T | G |
| 41 | 119 | 138 | 2913 | | | | | | | | | | | | G | G | H | M | T | Q | A | R | M | M | S | K | S | K | D | G | T | G | S | D |
| 42 | 121 | 140 | 68 | | | | | | | | | | | | | H | M | T | Q | A | R | M | M | S | K | S | K | D | G | T | G | S | D | D | K |

(56) References Cited

U.S. PATENT DOCUMENTS

| | | | |
|---|---|---|---|
| 2010/0261620 | A1 | 10/2010 | Almagro et al. |
| 2011/0092372 | A1 | 4/2011 | Almagro et al. |
| 2012/0108795 | A1 | 5/2012 | Kehoe |
| 2013/0100152 | A1 | 4/2013 | Feng |
| 2014/0017242 | A1 | 1/2014 | Williams |
| 2016/0376351 | A1 | 12/2016 | Adolfsson |
| 2017/0298119 | A1 | 10/2017 | Wollacott |

FOREIGN PATENT DOCUMENTS

| | | |
|---|---|---|
| WO | 2004/006955 A1 | 1/2004 |
| WO | 2004100898 A3 | 11/2004 |
| WO | 20006002177 A3 | 1/2006 |
| WO | 2007010040 A1 | 1/2007 |
| WO | 2007064919 A3 | 6/2007 |
| WO | 2009/085462 A1 | 7/2009 |
| WO | 2016/196726 A9 | 4/2017 |
| WO | 2018022786 A1 | 2/2018 |

OTHER PUBLICATIONS

Asuni, et al., Imnlunotherapy Targeting Pathological Tau Conformers in a Tangle Mouse Model Reduces Brain Pathology with Associated Functional Improvements, The Journal of Neuroscience, Aug. 22, 2007, pp. 9115-9129, vol. 27 Issue 34.

Barbie, et al., The Human Immunoglobulin Kappa Variable (IGKV) Genes and Joining (IGKJ) Segments, Exp Clin Immunogenet, Jun. 13, 1998, pp. 171-183, vol. 15.

Boutajangout, et al., Immunotherapy Targeting Pathological Tau Prevents Cognitive Decline in a New Tangle Mouse Model, The Journal of Neuroscience, Dec. 8, 2010, pp. 16559-16566, vol. 30 Issue 49.

Boutajangout, et al., Passive immunization targeting pathological phospho-tau protein in a mouse model reduces functional decline and clears tau aggregates from the brain, Journal of Neurochemistry, Jun. 1, 2011, pp. 658-667, vol. 118.

Brunden, et al., Advances in tau-focused drug discovery for Alzheimer's disease and related tauopathies, Nature Reviews | Drug Discovery, 2009, pp. 783-793, vol. 8.

Chai, et al., Passive Immunization with Anti-Tau Antibodies in Two Transgenic Models, The Journal of Biological Chemistry, Sep. 30, 2011, pp. 34457-34467, vol. 286 Issue 39.

Chothia, et al., Canonical Structures for the Hypervariable Regions of Immunoglobulins, J. Mol. Biol . . . , Apr. 23, 1987, pp. 901-917, vol. 196.

Clavaguera, et al., Transmission and spreading of tauopathy in transgenic mouse brain, Nature Cell Biology, Jun. 7, 2009, pp. 909-913, vol. 11 Issue 7.

Eduardo A. Padlan, A Possible Procedure for Reducing the Immunogenicity of Antibody Variable Domains While Preserving Theirligand-Binding Properties, Molecular Immunology, 1991, pp. 489-498, vol. 28 Issue 4/5.

Fishwild, et al., High-avidity human IgGK monoclonal antibodies from a novel strain of minilocus transgenic mice, Nature Biotechnology, May 1, 1996, pp. 845-851, vol. 14.

Fransson, et al., Human Framework Adaptation of a Mouse Anti-Human IL-13 Antibody., J. Mol. Biol., Mar. 10, 2010, pp. 214-231, vol. 398 Issue 2.

Frost, et al., Propagation of Tau Misfolding from the Outside to the Inside of a Cell, The Journal of Biological Chemistry, May 8, 2009, pp. 12845-12852, vol. 284 Issue 19.

Greenberg, et al., A preparation of Alzheimer paired helical filaments that displays distinct T proteins by polyacrylamide gel electrophoresis, Proc. Natl. Acad. Sci, Apr. 27, 1990, pp. 5827-5831, vol. 87.

Hanger, et al., Tau phosphorylation: the therapeutic challenge for neurodegenerative disease, Cell Press, Feb. 24, 2009, pp. 112-119, vol. 15 Issue 3.

Holmes, et al., Proteopathic tau seeding predicts tauopathy in vivo., Proc Natl Acad Sci, Sep. 26, 2014, pp. E4376-E4385, vol. 111 Issue 41.

Iba, et al., Synthetic Tau Fibrils Mediate Transmission of Neurofibrillary Tangles in a Transgenic Mouse Model of Alzheimer's-Like Tauopathy., The Journal of Neuroscience, Jan. 16, 2013, pp. 1024-1037, vol. 33 Issue 3.

Juan C. Almagro., Identification of differences in the specificity-determining residues of antibodies that recognize antigens of different size: implications for the rational design of antibody repertoires, Journal of Yiolecular Recognition, Dec. 17, 2003, pp. 132-143, vol. 17.

Knappik, et al., Fully Synthetic Human Combinatorial Antibody Libraries (HuCAL) Based on Modular Consensus Frameworks and CDRs Randomized with Trinucleotides, J. Mol. Biol., 2000, pp. 57-86, vol. 296.

Knight, et al., Pharmacodynamic enhancement of the antiplatelet antibody Fab abciximab by site-specific pegylation, Platelets; 2004, pp. 409-418, vol. 15 Issue 7.

Kohler, et al., Continuous cultures of fused cells secreting antibody of predefined specificity, Nature, Aug. 7, 1975, pp. 495-497, vol. 256.

Krebs, et al., High-throughput generation and engineering of recombinant human antibodies, Journal of Immunological Methods, Apr. 6, 2001, pp. 67-84, vol. 254.

Leong, et al., Adapting Pharmacokinetic Properties of a Humanized Anti-Interleukin-8 Antibody for Therapeutic Applications Using Site-Specific Pegylation, Cytokine, 2001, pp. 106-119, vol. 16 Issue 3.

Li, et al., Characterization of Two VQIXXK Motifs for Tau Fibrillization in Vitro., Bio chemistry, Dec. 19, 2006, pp. 15692-15701, vol. 45 Issue 51.

Lonberg, et al., Antigen-specific human antibodies from mice comprising four distinct genetic modifications, Nature, Apr. 28, 1994, pp. 856-859, vol. 368.

Mendez, et al., Functional transplant of megabase human immunoglobulin loci recapitulates human antibody response in mice, nature genetics, 1997, pp. 146-156, vol. 15.

Mercken, et al., Affinity Purification of Human T Proteins and the Construction of a Sensitive Sandwich Enzyme-Linked Immunosorbent Assay for Hilman T Detection, J. Neurochem., Jun. 25, 1991, pp. 548-553, vol. 58.

Morris, et al., The Many Faces of Tau, Neuron, May 12, 2011, pp. 410-426, vol. 70.

Peeraer, et al., Intracerebral injection of preformed synthetic tau fibrils initiates widespread tauopathy and neuronal loss in the brains of tau transgenic mice., Neurobiology of Disease, 2015, pp. 83-95, vol. 73.

Shi, et al., De Novo Selection of High-Affinity Antibodies from Synthetic Fab Libraries Displayed on Phage as pIX Fusion Proteins, J. Mol. Biol., Jan. 28, 2010, pp. 385-396, vol. 397 Issue 2.

Spillantini, et al., Tau protein pathology in neurodegenerative diseases, Trends Neurosci, 1998, pp. 428-433, vol. 21 Issue 10.

Timmerman, et al., Functional reconstruction and synthetic mimicry of a conformational epitope using CLIPSTM technology, Journal of Molecular Recognition, Aug. 1, 2007, pp. 283-299, vol. 20.

Yang, et al., Tailoring structure-function and pharmacokinetic properties of single-chain Fv proteins by site-specific PEGylation, Protein Engineering, 2003, pp. 761-770, vol. 16 Issue 10.

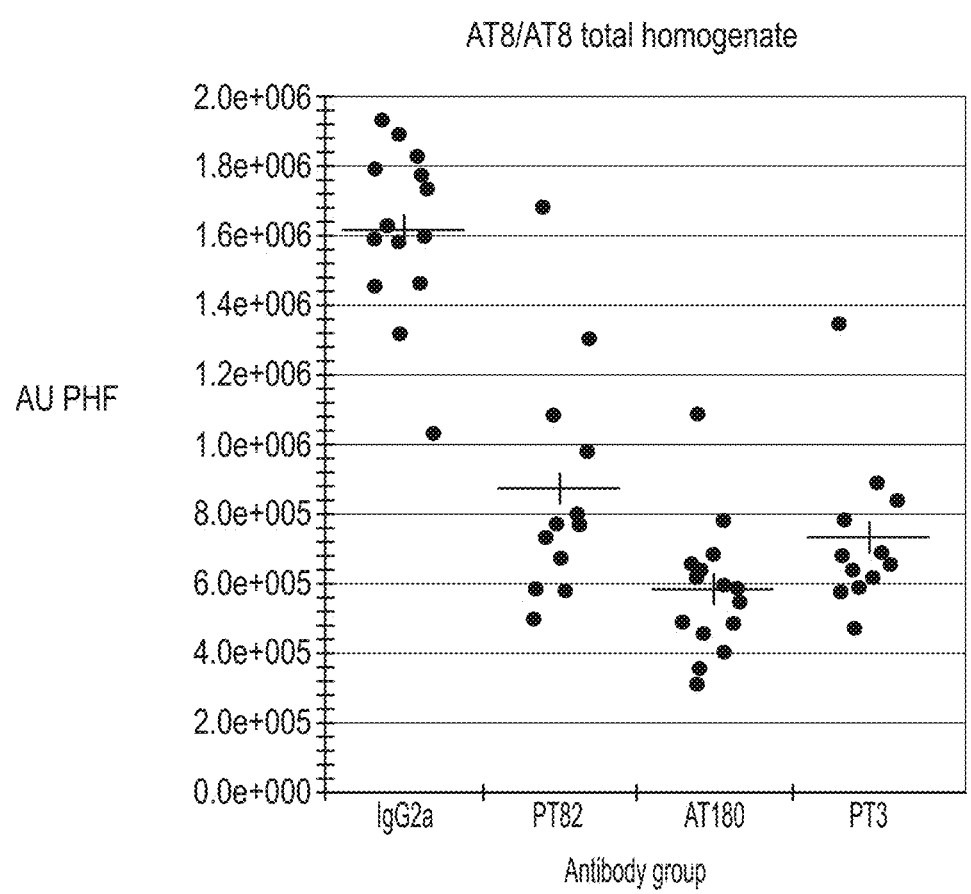

FIG. 7

| SEQ ID NO | | | PT82 | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|
| 33 | 103 | 122 | | A | E | E | A | G | I | G | D | T | P | S | L | E | D | E | A | A | G | H | M | | | | | | | | | | | | |
| 34 | 105 | 124 | 2904 | | E | | E | A | G | I | G | D | T | P | S | L | E | D | E | A | A | G | H | M | T | Q | | | | | | | | | |
| 35 | 107 | 126 | 2921 | | | | | | G | I | G | D | T | P | S | L | E | D | E | A | A | G | H | M | T | Q | A | R | | | | | | | |
| 36 | 109 | 128 | 2924 | | | | | | | | G | D | T | P | S | L | E | D | E | A | A | G | H | M | T | Q | A | R | M | M | | | | | | |
| 37 | 111 | 130 | 2927 | | | | | | | | | | T | P | S | L | E | D | E | A | A | G | H | M | T | Q | A | R | M | M | S | K | | | | | |
| 38 | 113 | 132 | 2927 | | | | | | | | | | | | S | L | E | D | E | A | A | G | H | M | T | Q | A | R | M | M | S | K | S | | | | | |
| 39 | 115 | 134 | 2919 | | | | | | | | | | | | | | E | D | E | A | A | G | H | M | T | Q | A | R | M | M | S | K | S | K | | | | |
| 40 | 117 | 136 | 2919 | | | | | | | | | | | | | | | | E | A | A | G | H | M | T | Q | A | R | M | M | S | K | S | K | D | G | | |
| 41 | 119 | 138 | 2913 | | | | | | | | | | | | | | | | | | | G | G | H | M | T | Q | A | R | M | M | S | K | S | K | D | G | T | G | S | D |
| 42 | 121 | 140 | 68 | | | | | | | | | | | | | | | | | | | | | H | M | T | Q | A | R | M | M | S | K | S | K | D | G | T | G | S | D | D | K |

SEQUENCE LISTING

```
<160> NUMBER OF SEQ ID NOS: 32

<210> SEQ ID NO 1
<211> LENGTH: 10
<212> TYPE: PRT
<213> ORGANISM: Artificial Sequence
<220> FEATURE:
<223> OTHER INFORMATION: PT82 VH CDR1

<400> SEQUENCE: 1

Gly Phe Thr Phe Ser Asn Tyr Trp Met Asn
1               5                   10
```

-continued

<210> SEQ ID NO 2
<211> LENGTH: 19
<212> TYPE: PRT
<213> ORGANISM: Artificial Sequence
<220> FEATURE:
<223> OTHER INFORMATION: PT82 VH CDR2

<400> SEQUENCE: 2

Gln Ile Arg Leu Gln Ser Asp Asn Tyr Ala Thr Arg Tyr Ala Glu Ser
1               5                   10                  15

Val Lys Gly

<210> SEQ ID NO 3
<211> LENGTH: 4
<212> TYPE: PRT
<213> ORGANISM: Artificial Sequence
<220> FEATURE:
<223> OTHER INFORMATION: PT82, PT1B778, PT1B779, PT1B780, PT1B781, and
      PT1B782 VH CDR3

<400> SEQUENCE: 3

Gly Thr Thr Tyr
1

<210> SEQ ID NO 4
<211> LENGTH: 11
<212> TYPE: PRT
<213> ORGANISM: Artificial Sequence
<220> FEATURE:
<223> OTHER INFORMATION: PT82 VL CDR1

<400> SEQUENCE: 4

Lys Ala Ser Gln Asn Val Gly Thr Ala Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: PT82, PT1B778, PT1B779, PT1B780, PT1B781, and
      PT1B782 VL CDR2

<400> SEQUENCE: 5

Ser Ala Ser Ile Arg Tyr Thr
1               5

<210> SEQ ID NO 6
<211> LENGTH: 9
<212> TYPE: PRT
<213> ORGANISM: Artificial Sequence
<220> FEATURE:
<223> OTHER INFORMATION: PT82, PT1B778, PT1B779, PT1B780, PT1B781, and
      PT1B782 VL CDR3

<400> SEQUENCE: 6

Gln Gln Phe Ser Ser Tyr Pro Tyr Thr
1               5

<210> SEQ ID NO 7
<211> LENGTH: 5
<212> TYPE: PRT
<213> ORGANISM: Artificial Sequence
<220> FEATURE:
<223> OTHER INFORMATION: PT1B778, PT1B779, PT1B780, PT1B781, and
      PT1B782 VH CDR1

```
<400> SEQUENCE: 7

Asn Tyr Trp Met Asn
1               5

<210> SEQ ID NO 8
<211> LENGTH: 19
<212> TYPE: PRT
<213> ORGANISM: Artificial Sequence
<220> FEATURE:
<223> OTHER INFORMATION: PT1B778 VH CDR2

<400> SEQUENCE: 8

Gln Ile Arg Leu Gln Ser Asp Asn Tyr Val Thr Arg Tyr Ala Ala Ser
1               5                   10                  15

Val Lys Gly

<210> SEQ ID NO 9
<211> LENGTH: 11
<212> TYPE: PRT
<213> ORGANISM: Artificial Sequence
<220> FEATURE:
<223> OTHER INFORMATION: PT1B778 VL CDR1

<400> SEQUENCE: 9

Lys Ala Ser Gln Asn Val Gly Thr Arg Val Ala
1               5                   10

<210> SEQ ID NO 10
<211> LENGTH: 19
<212> TYPE: PRT
<213> ORGANISM: Artificial Sequence
<220> FEATURE:
<223> OTHER INFORMATION: PT1B779 VH CDR2

<400> SEQUENCE: 10

Gln Ile Arg Leu Gln Asp Asp Asn Tyr Ala Thr Arg Tyr Ala Ala Ser
1               5                   10                  15

Val Lys Gly

<210> SEQ ID NO 11
<211> LENGTH: 11
<212> TYPE: PRT
<213> ORGANISM: Artificial Sequence
<220> FEATURE:
<223> OTHER INFORMATION: PT1B779, PT1B780, PT1B781, and PT1B782 VL CDR1

<400> SEQUENCE: 11

Lys Ala Ser Gln Asn Val Gly Thr Lys Val Ala
1               5                   10

<210> SEQ ID NO 12
<211> LENGTH: 19
<212> TYPE: PRT
<213> ORGANISM: Artificial Sequence
<220> FEATURE:
<223> OTHER INFORMATION: PT1B780 VH CDR2

<400> SEQUENCE: 12

Gln Ile Arg Leu Gln Ser Asp Asn Tyr Ala Thr Arg Tyr Ala Ala Ser
1               5                   10                  15

Val Lys Gly

<210> SEQ ID NO 13
```

```
<211> LENGTH: 19
<212> TYPE: PRT
<213> ORGANISM: Artificial Sequence
<220> FEATURE:
<223> OTHER INFORMATION: PT1B781 VH CDR2

<400> SEQUENCE: 13

Gln Ile Arg Leu Gln Arg Asp Asn Tyr Ala Thr Arg Tyr Ala Ala Ser
1               5                   10                  15

Val Lys Gly

<210> SEQ ID NO 14
<211> LENGTH: 19
<212> TYPE: PRT
<213> ORGANISM: Artificial Sequence
<220> FEATURE:
<223> OTHER INFORMATION: PT1B782 VH CDR2

<400> SEQUENCE: 14

Gln Ile Arg Leu Gln Tyr Asp Asn Tyr Ala Thr Arg Tyr Ala Ala Ser
1               5                   10                  15

Val Lys Gly

<210> SEQ ID NO 15
<211> LENGTH: 115
<212> TYPE: PRT
<213> ORGANISM: Artificial Sequence
<220> FEATURE:
<223> OTHER INFORMATION: PT82 VH Domain

<400> SEQUENCE: 15

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
                20                  25                  30

Trp Met Asn Trp Ile Arg Gln Ser Pro Glu Lys Gly Leu Glu Trp Val
            35                  40                  45

Ala Gln Ile Arg Leu Gln Ser Asp Asn Tyr Ala Thr Arg Tyr Ala Glu
        50                  55                  60

Ser Val Lys Gly Arg Phe Thr Ile Ser Arg Asp Glu Ser Lys Thr Ser
65                  70                  75                  80

Val Tyr Leu Gln Met Asn Asn Leu Arg Thr Glu Asp Thr Gly Ile Tyr
                85                  90                  95

Tyr Cys Thr Gly Gly Thr Thr Tyr Trp Gly Gln Gly Thr Leu Val Thr
                100                 105                 110

Val Ser Ala
        115

<210> SEQ ID NO 16
<211> LENGTH: 107
<212> TYPE: PRT
<213> ORGANISM: Artificial Sequence
<220> FEATURE:
<223> OTHER INFORMATION: PT82 VL Domain

<400> SEQUENCE: 16

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
                20                  25                  30

Val Ala Trp Tyr Gln Gln Lys Pro Gly Gln Ser Pro Lys Leu Leu Ile
```

```
                    35                  40                  45
Tyr Ser Ala Ser Ile Arg Tyr Thr Gly Val Pro Asp Arg Phe Thr Gly
         50                  55                  60
Ser Gly Ser Gly Thr Asp Phe Thr Leu Thr Ile Asn Tyr Met Gln Ser
 65                  70                  75                  80
Glu Asp Leu Ala Asp Tyr Phe Cys Gln Gln Phe Ser Ser Tyr Pro Tyr
                 85                  90                  95
Thr Phe Gly Gly Gly Thr Lys Leu Glu Ile Lys
             100                 105
```

<210> SEQ ID NO 17
<211> LENGTH: 115
<212> TYPE: PRT
<213> ORGANISM: Artificial Sequence
<220> FEATURE:
<223> OTHER INFORMATION: PT1B778 VH Domain

<400> SEQUENCE: 17

```
Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Ser Asn Tyr
             20                  25                  30
Trp Met Asn Trp Ile Arg Gln Ala Pro Gly Lys Gly Leu Glu Trp Val
         35                  40                  45
Gly Gln Ile Arg Leu Gln Ser Asp Asn Tyr Val Thr Arg Tyr Ala Ala
     50                  55                  60
Ser Val Lys Gly Arg Phe Thr Ile Ser Arg Asp Asp Ser Lys Asn Ser
 65                  70                  75                  80
Val Tyr Leu Gln Met Asn Ser Leu Lys Thr Glu Asp Thr Ala Val Tyr
                 85                  90                  95
Tyr Cys Thr Gly Gly Thr Thr Tyr Trp Gly Gln Gly Thr Leu Val Thr
             100                 105                 110
Val Ser Ser
         115
```

<210> SEQ ID NO 18
<211> LENGTH: 107
<212> TYPE: PRT
<213> ORGANISM: Artificial Sequence
<220> FEATURE:
<223> OTHER INFORMATION: PT1B778 VL Domain

<400> SEQUENCE: 18

```
Asp Ile Gln Met Thr Gln Ser Pro Ser Phe Leu Ser Ala Ser Val Gly
  1               5                  10                  15
Asp Arg Val Thr Ile Thr Cys Lys Ala Ser Gln Asn Val Gly Thr Arg
             20                  25                  30
Val Ala Trp Tyr Gln Gln Lys Pro Gly Lys Ala Pro Lys Leu Leu Ile
         35                  40                  45
Tyr Ser Ala Ser Ile Arg Tyr Thr Gly Val Pro Ser Arg Phe Ser Gly
     50                  55                  60
Ser Gly Ser Gly Thr Glu Phe Thr Leu Thr Ile Ser Ser Met Gln Pro
 65                  70                  75                  80
Glu Asp Phe Ala Thr Tyr Tyr Cys Gln Gln Phe Ser Ser Tyr Pro Tyr
                 85                  90                  95
Thr Phe Gly Gln Gly Thr Lys Leu Glu Ile Lys
             100                 105
```

<210> SEQ ID NO 19
<211> LENGTH: 115
<212> TYPE: PRT
<213> ORGANISM: Artificial Sequence
<220> FEATURE:
<223> OTHER INFORMATION: PT1B779 VH Domain

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Ile Arg Gln Ala Pro Gly Lys Gly Leu Glu Trp Val
        35                  40                  45

Gly Gln Ile Arg Leu Gln Asp Asp Asn Tyr Ala Thr Arg Tyr Ala Ala
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Ala Val Tyr
                85                  90                  95

Tyr Cys Thr Gly Gly Thr Thr Tyr Trp Gly Gln Gly Thr Leu Val Thr
            100                 105                 110

Val Ser Ser
        115
```

<210> SEQ ID NO 20
<211> LENGTH: 107
<212> TYPE: PRT
<213> ORGANISM: Artificial Sequence
<220> FEATURE:
<223> OTHER INFORMATION: PT1B779 and PT1B781 VL Domain

<400> SEQUENCE: 20

```
Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Lys
            20                  25                  30

Val Ala Trp Tyr Gln Gln Lys Pro Gly Lys Ala Pro Lys Leu Leu Ile
        35                  40                  45

Tyr Ser Ala Ser Ile Arg Tyr Thr Gly Val Pro Ser Arg Phe Ser Gly
    50                  55                  60

Ser Gly Ser Gly Thr Glu Phe Thr Leu Thr Ile Ser Ser Met Gln Pro
65                  70                  75                  80

Glu Asp Phe Ala Thr Tyr Tyr Cys Gln Gln Phe Ser Ser Tyr Pro Tyr
                85                  90                  95

Thr Phe Gly Gln Gly Thr Lys Leu Glu Ile Lys
            100                 105
```

<210> SEQ ID NO 21
<211> LENGTH: 115
<212> TYPE: PRT
<213> ORGANISM: Artificial Sequence
<220> FEATURE:
<223> OTHER INFORMATION: PT1B780 VH Domain

<400> SEQUENCE: 21

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
```

```
                    20                  25                  30

Trp Met Asn Trp Ile Arg Gln Ala Pro Gly Lys Gly Leu Glu Trp Val
            35                  40                  45

Gly Gln Ile Arg Leu Gln Ser Asp Asn Tyr Ala Thr Arg Tyr Ala Ala
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                    85                  90                  95

Tyr Cys Thr Gly Gly Thr Thr Tyr Trp Gly Gln Gly Thr Leu Val Thr
                100                 105                 110

Val Ser Ser
        115

<210> SEQ ID NO 22
<211> LENGTH: 107
<212> TYPE: PRT
<213> ORGANISM: Artificial Sequence
<220> FEATURE:
<223> OTHER INFORMATION: PT1B780 VL Domain

<400> SEQUENCE: 22

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Lys
                20                  25                  30

Val Ala Trp Tyr Gln Gln Lys Pro Gly Lys Ala Pro Lys Leu Leu Ile
            35                  40                  45

Tyr Ser Ala Ser Ile Arg Tyr Thr Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Phe Ser Ser Tyr Pro Tyr
                85                  90                  95

Thr Phe Gly Gln Gly Thr Lys Leu Glu Ile Lys
                100                 105

<210> SEQ ID NO 23
<211> LENGTH: 115
<212> TYPE: PRT
<213> ORGANISM: Artificial Sequence
<220> FEATURE:
<223> OTHER INFORMATION: PT1B781 VH Domain

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Trp Met Asn Trp Ile Arg Gln Ala Pro Gly Lys Gly Leu Glu Trp Val
            35                  40                  45

Gly Gln Ile Arg Leu Gln Arg Asp Asn Tyr Ala Thr Arg Tyr Ala Ala
        50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Ala Val Tyr
                    85                  90                  95
```

Tyr Cys Thr Gly Gly Thr Thr Tyr Trp Gly Gln Gly Thr Leu Val Thr
            100                 105                 110

Val Ser Ser
        115

<210> SEQ ID NO 24
<211> LENGTH: 115
<212> TYPE: PRT
<213> ORGANISM: Artificial Sequence
<220> FEATURE:
<223> OTHER INFORMATION: PT1B782 VH Domain

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Ile Arg Gln Ala Pro Gly Lys Gly Leu Glu Trp Val
            35                  40                  45

Gly Gln Ile Arg Leu Gln Tyr Asp Asn Tyr Ala Thr Arg Tyr Ala Ala
        50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Ala Val Tyr
                85                  90                  95

Tyr Cys Thr Gly Gly Thr Thr Tyr Trp Gly Gln Gly Thr Leu Val Thr
            100                 105                 110

Val Ser Ser
        115

<210> SEQ ID NO 25
<211> LENGTH: 107
<212> TYPE: PRT
<213> ORGANISM: Artificial Sequence
<220> FEATURE:
<223> OTHER INFORMATION: PT1B782 VL Domain

<400> SEQUENCE: 25

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Lys
            20                  25                  30

Val Ala Trp Tyr Gln Gln Lys Pro Gly Lys Ala Pro Lys Leu Leu Ile
            35                  40                  45

Tyr Ser Ala Ser Ile Arg Tyr Thr Gly Val Pro Ser Arg Phe Ser Gly
        50                  55                  60

Ser Gly Ser Gly Thr Glu Phe Thr Leu Thr Ile Ser Ser Met Gln Pro
65                  70                  75                  80

Glu Asp Phe Ala Thr Tyr Tyr Cys Gln Gln Phe Ser Ser Tyr Pro Tyr
                85                  90                  95

Thr Phe Gly Gln Gly Thr Lys Leu Glu Ile Lys
            100                 105

<210> SEQ ID NO 26
<211> LENGTH: 352
<212> TYPE: PRT
<213> ORGANISM: Artificial Sequence
<220> FEATURE:
<223> OTHER INFORMATION: 0N3R Tau

<400> SEQUENCE: 26

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
    195                 200                 205

Lys His Gln Pro Gly Gly Gly Lys Val Gln Ile Val Tyr Lys Pro Val
210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
    275                 280                 285

Phe Arg Glu Asn Ala Lys Ala Lys Thr Asp His Gly Ala Glu Ile Val
290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350
```

<210> SEQ ID NO 27
<211> LENGTH: 381
<212> TYPE: PRT
<213> ORGANISM: Artificial Sequence
<220> FEATURE:
<223> OTHER INFORMATION: 1N3R Tau

<400> SEQUENCE: 27

Met Ala Glu Pro Arg Gln Glu Phe Glu Val Met Glu Asp His Ala Gly

```
            1               5                   10                  15
        Thr Tyr Gly Leu Gly Asp Arg Lys Asp Gln Gly Gly Tyr Thr Met His
                        20                  25                  30

Gln Asp Gln Glu Gly Asp Thr Asp Ala Gly Leu Lys Glu Ser Pro Leu
                        35                  40                  45

Gln Thr Pro Thr Glu Asp Gly Ser Glu Pro Gly Ser Glu Thr Ser
        50                      55                  60

Asp Ala Lys Ser Thr Pro Thr Ala Glu Ala Glu Ala Gly Ile Gly
        65                      70                  75              80

Asp Thr Pro Ser Leu Glu Asp Glu Ala Ala Gly His Val Thr Gln Ala
                            85                  90                  95

Arg Met Val Ser Lys Ser Lys Asp Gly Thr Gly Ser Asp Asp Lys Lys
                        100                 105                 110

Ala Lys Gly Ala Asp Gly Lys Thr Lys Ile Ala Thr Pro Arg Gly Ala
                        115                 120                 125

Ala Pro Pro Gly Gln Lys Gly Gln Ala Asn Ala Thr Arg Ile Pro Ala
                        130                 135                 140

Lys Thr Pro Pro Ala Pro Lys Thr Pro Pro Ser Ser Gly Glu Pro Pro
        145                 150                 155                 160

Lys Ser Gly Asp Arg Ser Gly Tyr Ser Ser Pro Gly Ser Pro Gly Thr
                        165                 170                 175

Pro Gly Ser Arg Ser Arg Thr Pro Ser Leu Pro Thr Pro Pro Thr Arg
                        180                 185                 190

Glu Pro Lys Lys Val Ala Val Val Arg Thr Pro Pro Lys Ser Pro Ser
                        195                 200                 205

Ser Ala Lys Ser Arg Leu Gln Thr Ala Pro Val Pro Met Pro Asp Leu
        210                 215                 220

Lys Asn Val Lys Ser Lys Ile Gly Ser Thr Glu Asn Leu Lys His Gln
        225                 230                 235                 240

Pro Gly Gly Gly Lys Val Gln Ile Val Tyr Lys Pro Val Asp Leu Ser
                        245                 250                 255

Lys Val Thr Ser Lys Cys Gly Ser Leu Gly Asn Ile His His Lys Pro
                        260                 265                 270

Gly Gly Gly Gln Val Glu Val Lys Ser Glu Lys Leu Asp Phe Lys Asp
                        275                 280                 285

Arg Val Gln Ser Lys Ile Gly Ser Leu Asp Asn Ile Thr His Val Pro
                        290                 295                 300

Gly Gly Gly Asn Lys Lys Ile Glu Thr His Lys Leu Thr Phe Arg Glu
        305                 310                 315                 320

Asn Ala Lys Ala Lys Thr Asp His Gly Ala Glu Ile Val Tyr Lys Ser
                        325                 330                 335

Pro Val Val Ser Gly Asp Thr Ser Pro Arg His Leu Ser Asn Val Ser
                        340                 345                 350

Ser Thr Gly Ser Ile Asp Met Val Asp Ser Pro Gln Leu Ala Thr Leu
                        355                 360                 365

Ala Asp Glu Val Ser Ala Ser Leu Ala Lys Gln Gly Leu
        370                 375                 380

<210> SEQ ID NO 28
<211> LENGTH: 410
<212> TYPE: PRT
<213> ORGANISM: Artificial Sequence
<220> FEATURE:
<223> OTHER INFORMATION: 2N3R Tau
```

<400> SEQUENCE: 28

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Val Tyr Lys Pro Val Asp Leu Ser Lys Val Thr
        275                 280                 285

Ser Lys Cys Gly Ser Leu Gly Asn Ile His His Lys Pro Gly Gly Gly
    290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
                325                 330                 335

Asn Lys Lys Ile Glu Thr His Lys Leu Thr Phe Arg Glu Asn Ala Lys
            340                 345                 350

Ala Lys Thr Asp His Gly Ala Glu Ile Val Tyr Lys Ser Pro Val Val
        355                 360                 365

Ser Gly Asp Thr Ser Pro Arg His Leu Ser Asn Val Ser Ser Thr Gly
    370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410
```

<210> SEQ ID NO 29
<211> LENGTH: 383
<212> TYPE: PRT
<213> ORGANISM: Artificial Sequence
<220> FEATURE:
<223> OTHER INFORMATION: 0N4R Tau

<400> SEQUENCE: 29

```
Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
             20                  25                  30

Gln Asp Gln Glu Gly Asp Thr Asp Ala Gly Leu Lys Ala Glu Glu Ala
         35                  40                  45

Gly Ile Gly Asp Thr Pro Ser Leu Glu Asp Glu Ala Ala Gly His Val
     50                  55                  60

Thr Gln Ala Arg Met Val Ser Lys Ser Lys Asp Gly Thr Gly Ser Asp
 65                  70                  75                  80

Asp Lys Lys Ala Lys Gly Ala Asp Gly Lys Thr Lys Ile Ala Thr Pro
                 85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365
```

```
Thr Leu Ala Asp Glu Val Ser Ala Ser Leu Ala Lys Gln Gly Leu
    370                 375                 380

<210> SEQ ID NO 30
<211> LENGTH: 441
<212> TYPE: PRT
<213> ORGANISM: Artificial Sequence
<220> FEATURE:
<223> OTHER INFORMATION: 1N4R Tau

<400> SEQUENCE: 30

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350
```

-continued

Lys Ile Gly Ser Leu Asp Asn Ile Thr His Val Pro Gly Gly Gly Asn
              355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
              405                 410                 415

Ile Asp Met Val Asp Ser Pro Gln Leu Ala Thr Leu Ala Asp Glu Val
              420                 425                 430

Ser Ala Ser Leu Ala Lys Gln Gly Leu
              435                 440

<210> SEQ ID NO 31
<211> LENGTH: 441
<212> TYPE: PRT
<213> ORGANISM: Artificial Sequence
<220> FEATURE:
<223> OTHER INFORMATION: 2N4R Tau

<400> SEQUENCE: 31

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

```
Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
        290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
        370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
            435                 440

<210> SEQ ID NO 32
<211> LENGTH: 6
<212> TYPE: PRT
<213> ORGANISM: Artificial Sequence
<220> FEATURE:
<223> OTHER INFORMATION: Binding epitope of PT82 to tau

<400> SEQUENCE: 32

Ala Gly His Val Thr Gln
1               5
```

ANTI-PHF-TAU ANTIBODIES AND USES THEREOF

This application claims priority to U.S. Provisional Application No. 62/638,535 with a filing date of Mar. 5, 2018. The provisional application is incorporated by reference in its entirety.

This application contains a sequence listing, which is submitted electronically via EFS-Web as an ASCII formatted seguence listing with a file name "JAB6124 Substitute Seguence Listing (1485220.1)," creation date of Feb. 21, 2020, and having a size of 39kB. The sequence listing submitted via EFS-Web is part of the specification and is herein incorporated by reference in its entirety.

FIELD OF THE INVENTION

The present invention relates to anti-PHF-tau antibodies, and methods of making and using them.

BACKGROUND OF THE INVENTION

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in ethnic groups worldwide and presents a major present and future public health problem.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles of paired helical filaments, are generally found in several areas of the human brain important for memory and cognitive function in patients with AD.

The main protein component of the neurofibrillary degeneration in AD and several other neurodegenerative diseases is a hyperphosphorylated form of the microtubule associated protein tau. Developing therapeutics preventing or clearing tau aggregation has been of interest for many years, but candidate drugs, including anti-aggregation compounds and kinase inhibitors, have only just entered in clinical testing (Brunden, et al. *Nat Rev Drug Discov* 8:783-93, 2009).

Recently, preclinical evidence has been produced in transgenic tau mouse models that active and passive immunization for tau can have therapeutic potential (Chai, et al. *J Biol Chem* 286:34457-67, 2011, Boutajangout, et al. *J Neurochem* 118:658-67, 2011, Boutajangout, et al. *J Neurosci* 30:16559-66, 2010, Asuni, et al. *J Neurosci* 27:9115-29, 2007). A tauopathy transmission and spreading hypothesis has recently been described and is based on the Braak stages of tauopathy progression in human brain and tauopathy spreading after tau aggregate injections in preclinical tau models (Frost, et al. *J Biol Chem* 284:12845-52, 2009, Clavaguera, et al. *Nat Cell Biol* 11:909-13, 2009). Thus, there is a need for therapeutics to prevent tau aggregation and tauopathy progression to treat AD and other neurodegenerative diseases.

SUMMARY OF THE INVENTION

In one general aspect, the invention relates to an isolated antibody, preferably an isolated monoclonal antibody, or an antigen-binding fragment thereof wherein the antibody or antigen-binding fragment thereof binds PHF-tau, preferably human PHF-tau.

In one embodiment, a monoclonal antibody or an antigen-binding fragment thereof of the invention has a heavy chain comprising an HCDR1 of SEQ ID NO:1 or 7; an HCDR2 of SEQ ID NO:2, 8, 10, 12, 13 or 14; and an HCDR3 of SEQ ID NO:3. In another embodiment, a monoclonal antibody of the invention has a light chain comprising an LCDR1 of SEQ ID NO:4, 9 or 11; an LCDR2 of SEQ ID NO:5; and an LCDR3 of SEQ ID NO:6. In other embodiments, a monoclonal antibody of the invention comprises a CDR that is at least 97% identical, at least 98% identical or at least 99% identical to a CDR of any of SEQ ID NOs:1, 2, 3, 4, 5, 6, 7, 8, 9, 10, 11, 12, 13 and 14.

In another embodiment, a monoclonal antibody or an antigen-binding fragment thereof of the invention comprises a heavy chain variable region comprising an amino acid sequence at least 80%, at least 85%, at least 90%, at least 95%, at least 97%, at least 98%, at least 99% or 100% identical to any of SEQ ID NOs:15, 17, 19, 21, 23 and 24. In another embodiment, a monoclonal antibody or an antigen-binding fragment thereof of the invention comprises a light chain variable region comprising an amino acid sequence at least 80%, at least 85%, at least 90%, at least 95%, at least 97%, at least 98%, at least 99% or 100% identical to any of SEQ ID NOs: 16, 18, 20, 22 and 25.

In another embodiment, an isolated antibody or an antigen-binding fragment thereof of the invention further comprises a constant region, such as a human or mouse heavy chain IgG constant region, and a human or mouse antibody light chain kappa or lambda constant region.

In another general aspect, the invention relates to an isolated nucleic acid encoding an antibody or an antigen-binding fragment thereof of the invention.

In another general aspect, the invention relates to a vector comprising an isolated nucleic acid encoding an antibody or an antigen-binding fragment thereof of the invention.

In another general aspect, the invention relates to a host cell comprising an isolated nucleic acid encoding an antibody or an antigen-binding fragment thereof of the invention.

In another general aspect, the invention relates to a pharmaceutical composition comprising an isolated antibody or an antigen-binding fragment thereof of the invention and a pharmaceutically acceptable carrier.

In another general aspect, the invention relates to a method of reducing pathological tau aggregation or spreading of tauopathy in a subject in need thereof, comprising administering to the subject a pharmaceutical composition of the invention. The tauopathy includes, but is not limited to, one or more selected from the group consisting of Alzheimer's disease (including familial Alzheimer's disease and sporadic Alzheimer's disease), frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Sträussler-Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, postencephalitic parkinsonism, chronic traumatic encephalopathy, and dementia pugulistica (boxing disease).

Preferably, the tauopathy is Alzheimer's disease (including familial Alzheimer's disease and sporadic Alzheimer's disease), FTDP-17 or progressive supranuclear palsy.

Most preferably, the tauopathy is Alzheimer's disease (including familial Alzheimer's disease and sporadic Alzheimer's disease).

In another general aspect, the invention relates to a method of producing an antibody or an antigen-binding fragment thereof of the invention, comprising culturing a cell comprising a nucleic acid encoding the antibody or antigen-binding fragment under conditions to produce the antibody or antigen-binding fragment thereof, and recovering the antibody or antigen-binding fragment thereof from the cell or cell culture.

In another general aspect, the invention relates to a method of producing a pharmaceutical composition comprising an antibody or antigen-binding fragment thereof of the invention, comprising combining the antibody or antigen-binding fragment thereof with a pharmaceutically acceptable carrier to obtain the pharmaceutical composition.

In another general aspect, the invention relates to a method of detecting the presence of PHF-tau in a subject or a method of diagnosing a tauopathy in a subject by detecting the presence of PHF-tau in the subject using an antibody or antigen-binding fragment thereof of the invention.

Other aspects, features and advantages of the invention will be apparent from the following disclosure, including the detailed description of the invention and its preferred embodiments and the appended claims.

BRIEF DESCRIPTION OF THE FIGURES

The foregoing summary, as well as the following detailed description of the invention, will be better understood when read in conjunction with the appended drawings. It should be understood that the invention is not limited to the precise embodiments shown in the drawings.

FIGS. 5A-5B show efficacy of PT82 as compared to AT180 and PT3 antibodies in the in vivo ePHF injection model when either (A) total homogenate or (B) the insoluble fraction was analyzed.

FIG. 7 shows epitope mapping data using linear peptide mapping of PT82.

DETAILED DESCRIPTION OF THE INVENTION

Figure 1A:
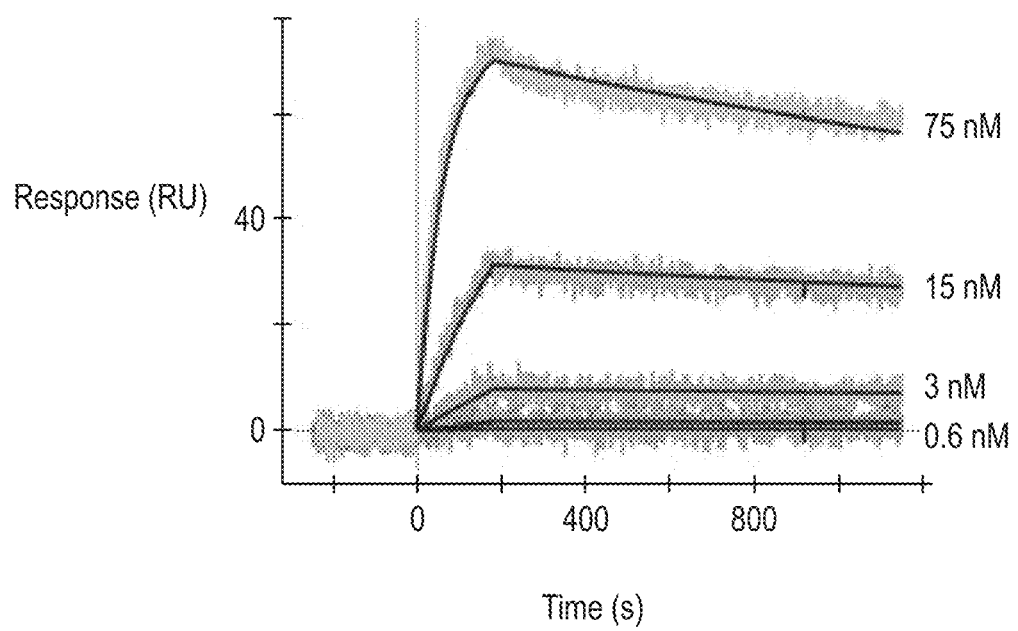
FIGS. 1A-1C show binding of recombinantly expressed PT82 mAb or its Fab fragment to PHF-tau and soluble-tau analyzed by surface plasmon resonance (SPR), wherein concentration of antibody or Fab are indicated next to the respective sensorgrams (75 nM; 15 nM; 3 nM; 0.6 nM). Binding of (A) mAb to PHF (B) Fab to PHF and (C) Fab to 2N4R Tau is shown.

The term "antibodies" as used herein is meant in a broad sense and includes immunoglobulin or antibody molecules including polyclonal antibodies, monoclonal antibodies including murine, human, human-adapted, humanized and chimeric monoclonal antibodies and antibody fragments.

In general, antibodies are proteins or peptide chains that exhibit binding specificity to a specific antigen. Antibody structures are well known Immunoglobulins can be assigned to five major classes, namely IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species can be assigned to one of two clearly distinct types, namely kappa (κ) and lambda (i), based on the amino acid sequences of their constant domains.

The term "antibody fragments" means a portion of an intact antibody. Examples of antibody fragments include Fab, Fab', F(ab')$_2$ and Fv fragments, CDR, antigen-binding site, heavy or light chain variable region, diabodies, single chain antibody molecules and multispecific antibodies formed from at least two intact antibodies or fragments thereof.

An immunoglobulin light or heavy chain variable region consists of a "framework" region interrupted by "antigen-binding sites". The antigen-binding sites are defined using various terms as follows: (i) Complementarity Determining Regions (CDRs) are based on sequence variability (Wu and Kabat *J Exp Med* 132:211-50, 1970). Generally, the antigen-binding site has three CDRs in each variable region (HCDR1, HCDR2 and HCDR3 in heavy chain variable region (VH) and LCDR1, LCDR2 and LCDR3 in light chain variable region (VL)) (Kabat et al., Sequences of Proteins of Immunological Interest, 5th Ed. Public Health Service, National Institutes of Health, Bethesda, Md., 1991). (ii) The term "hypervariable region", "HVR", or "HV" refers to the regions of an antibody variable domain which are hypervariable in structure as defined by Chothia and Lesk (Chothia and Lesk *J Mol Biol* 196:901-17, 1987). Generally, the antigen-binding site has three hypervariable regions in each VH (H1, H2, H3) and VL (L1, L2, L3). Chothia and Lesk refer to structurally conserved HVs as "canonical structures". Numbering systems as well as annotation of CDRs and HVs have recently been revised by Abhinandan and Martin (Abhinandan and Martin *Mol Immunol* 45:3832-9, 2008). (iii) Another definition of the regions that form the antigen-binding site has been proposed by Lefranc (Lefranc, et al. *Dev Comp Immunol* 27:55-77, 2003) based on the comparison of V domains from immunoglobulins and T-cell receptors. The International ImMunoGeneTics (IMGT) database provides a standardized numbering and definition of these regions. The correspondence between CDRs, HVs and IMGT delineations is described in Lefranc et al., supra. (iv) The antigen-binding site can also be delineated based on Specificity Determining Residue Usage (SDRU) (Almagro *J Mol Recognit* 17:132-43, 2004), where Specificity Determining Residues (SDR), refers to amino acid residues of an immunoglobulin that are directly involved in antigen contact.

"Framework" or "framework sequence" are the remaining sequences within the variable region of an antibody other than those defined to be antigen-binding site sequences. Because the exact definition of an antigen-binding site can be determined by various delineations as described above, the exact framework sequence depends on the definition of the antigen-binding site.

The term "monoclonal antibody" (mAb) as used herein means an antibody (or antibody fragment) obtained from a population of substantially homogeneous antibodies. Monoclonal antibodies are highly specific, typically being directed against a single antigenic determinant.

The term "epitope" as used herein means a portion of an antigen to which an antibody specifically binds. Epitopes usually consist of chemically active (such as polar, nonpolar or hydrophobic) surface groupings of moieties such as amino acids, phosphorylated amino acids or polysaccharide side chains and can have specific three-dimensional structural characteristics, as well as specific charge characteristics. An epitope can be linear in nature or can be a discontinuous epitope, e.g., a conformational epitope, which is formed by a spatial relationship between non-contiguous amino acids of an antigen rather than a linear series of amino acids. A conformational epitope includes epitopes resulting from folding of an antigen, where amino acids from differing portions of the linear sequence of the antigen come in close proximity in 3-dimensional space.

Tau is an abundant central and peripheral nervous system protein having multiple well known isoforms. In the human CNS, six major tau isoforms ranging in size from 352 to 441 exist due to alternative splicing (Hanger, et al. *Trends Mol Med* 15:112-9, 2009). These isoforms differ from each other by the regulated inclusion of 0-2 N-terminal inserts, and 3 or 4 tandemly arranged microtubule-binding repeats, and are referred to as 0N3R (SEQ ID NO: 26), 1N3R (SEQ ID NO: 27), 2N3R (SEQ ID NO: 28), 0N4R (SEQ ID NO: 29), 1N4R (SEQ ID NO: 30) and 2N4R (SEQ ID NO: 31). The terms "control tau" and "soluble-tau" as used interchangeably herein refer to the tau isoform of SEQ ID NO: 31 that is devoid of phosphorylation and other post-translational modifications.

Tau binds microtubules and regulates transport of cargo through cells, a process that can be modulated by tau phosphorylation. In AD and related disorders abnormal phosphorylation of tau is prevalent and thought to precede and/or trigger aggregation of tau into fibrils, termed paired helical filaments (PHF). The major constituent of PHF is hyperphosphorylated tau. The term "paired helical filament-tau" or "PHF-tau" as used herein refers to well known tau aggregates in paired helical filaments. Two major regions in PHF structure are evident in electron microscopy, the fuzzy coat and the core filament; the fuzzy coat being sensitive to proteolysis and located outside of the filaments, and the protease resistant core of filaments forming the backbone of PHFs (Wischik, et al. *Proc Natl Acad Sci USA* 85:4884-8, 1988).

"Antibodies that bind PHF-tau" as used herein refers to antibodies that bind PHF-tau as assessed on western blot. Typically, antibody binding to PHF-tau can be assessed after Coomassie stain of about 500 ng of PHF-tau after 1 hour blocking in 5% (w/v) nonfat dry milk (NFDM) TBS-T, 0.05% Tween-20. Antibodies that bind PHF-tau optionally do not bind control tau (SEQ ID NO: 31) as measured by western blot when tested under antigen loading condition where both control tau and PHF-tau is detected equally by tau antibodies that have no preference for PHF-tau epitopes (e.g. antibody HT7, (ThermoScientific, Rockford, Ill.) (Mercken, et al. *J Neurochem* 58:548-53, 1992). Such exemplary antigen loading conditions are 500 ng PHF-tau and 200 ng control tau.

Conventional well known one and three-letter amino acid codes are used herein.

Compositions of Matter

The present invention relates to anti-PHF-tau antibodies and uses of such antibodies. Such anti-PHF-tau antibodies can have the properties of binding a phosphorylated epitope on PHF-tau or binding to a non-phosphorylated epitope on PHF-tau. Anti-PHF-tau antibodies can be useful as therapeutics, and as research or diagnostic reagents to detect PHF-tau in biological samples, for example in tissues or cells.

In preferred embodiments, antibodies of the invention have the sequences shown in Table 1. PT82 is a mouse monoclonal antibody and PT1B778, PT1B779, PT1B780, PT1B781 and PT1B782 are humanized versions of PT82. CDRs are underlined in the variable region sequences. The bolded amino acids in the CDRs of the humanized monoclonal antibodies indicate a substitution as compared to the PT82 CDR sequence.

TABLE 1

| mAb | Name | | SEQ ID NO | Sequence |
|---|---|---|---|---|
| PT82 | | | | |
| | $V_H$ | CDR1 | 1 | GFTFSNYWMN |
| | | CDR2 | 2 | QIRLQSDNYATRYAESVKG |
| | | CDR3 | 3 | GTTY |
| | $V_H$ Domain | | 15 | EVKLEESGGGLVQPGGSMKLSCVAS<u>GFTFSNYWMN</u>WIRQSPE KGLEWVA<u>QIRLQSDNYATRYAESVKG</u>RFTISRDESKTSVYLQ MNNLRTEDTGIYYCTGG<u>TTY</u>WGQGTLVTVSA |
| | $V_L$ | CDR1 | 4 | KASQNVGTAVA |
| | | CDR2 | 5 | SASIRYT |
| | | CDR3 | 6 | QQFSSYPYT |
| | $V_L$ Domain | | 16 | DIVMTQSQKFMSTSVGDRVSITC<u>KASQNVGTAVA</u>WYQQKPGQ SPKLLIY<u>SASIRYT</u>GVPDRFTGSGSGTDFTLTINYMQSEDLA DYFC<u>QQFSSYPYT</u>FGGGTKLEIK |
| PT1B778 | | | | |
| | $V_H$ | CDR1 | 7 | NYWMN |
| | | CDR2 | 8 | QIRLQSDNYVTRYAASVKG |
| | | CDR3 | 3 | GTTY |

TABLE 1-continued

| mAb | Name | | SEQ ID NO | Sequence |
|---|---|---|---|---|
| | V$_H$ Domain | | 17 | EVQLVESGGGLVQPGGSLRLSCAASGFTFS<u>NYWMN</u>WIRQAPG KGLEWVG<u>QIRLQSDNYVTRYAA</u>SVKGRFTISRDDSKNSVYLQ MNSLKTEDTAVYYCTG<u>GTTY</u>WGQGTLVTVSS |
| | V$_L$ | CDR1 | 9 | KASQNVGTRVA |
| | | CDR2 | 5 | SASIRYT |
| | | CDR3 | 6 | QQFSSYPYT |
| | V$_L$ Domain | | 18 | DIQMTQSPSFLSASVGDRVTITC<u>KASQNVGT RV</u>AWYQQKPGKAPKLLIY<u>SASIRYT</u>GVPSRFSGSGSGTEFTL TISSMQPEDFATYYC<u>QQFSSYPYT</u>FGQGTKLEIK |
| PT1B779 | V$_H$ | CDR1 | 7 | NYWMN |
| | | CDR2 | 10 | QIRLQDDNYATRYAASVKG |
| | | CDR3 | 3 | GTTY |
| | V$_H$ Domain | | 19 | EVQLVESGGGLVQPGGSLRLSCAASGFTFS<u>N YWMN</u>WIRQAPGKGLEWVG<u>QIRLQDDNYATRYAA</u>SVKGRFTIS RDDSKNSVYLQMNSLKTEDTAVYYCTG<u>GTTY</u>WGQGTLVTVSS |
| | V$_L$ | CDR1 | 11 | KASQNVGTKVA |
| | | CDR2 | 5 | SASIRYT |
| | | CDR3 | 6 | QQFSSYPYT |
| | V$_L$ Domain | | 20 | DIQMTQSPSFLSASVGDRVTITC<u>KASQNVGTKVA</u>WYQQKPGK APKLLIY<u>SASIRYT</u>GVPSRFSGSGSGTEFTLTISSMQPEDFA TYYC<u>QQFSSYPYT</u>FGQGTKLEIK |
| PT1B780 | V$_H$ | CDR1 | 7 | NYWMN |
| | | CDR2 | 12 | QIRLQSDNYATRYAASVKG |
| | | CDR3 | 3 | GTTY |
| | V$_H$ Domain | | 21 | EVQLVESGGGLVQPGGSLRLSCAASGFTFS<u>NYWMN</u>WIRQAPG KGLEWVG<u>QIRLQSDNYATRYAA</u>SVKGRFTISRDDSKNSLYLQ MNSLKTEDTAVYYCTG<u>GTTY</u>WGQGTLVTVSS |
| | V$_L$ | CDR1 | 11 | KASQNVGTKVA |
| | | CDR2 | 5 | SASIRYT |
| | | CDR3 | 6 | QQFSSYPYT |
| | V$_L$ Domain | | 22 | DIQMTQSPSFLSASVGDRVTITC<u>KASQNVGTKVA</u>WYQQKPGK APKLLIY<u>SASIRYT</u>GVPSRFSGSGSGTEFTLTISSLQPEDFA TYYC<u>QQFSSYPYT</u>FGQGTKLEIK |
| PT1B781 | V$_H$ | CDR1 | 7 | NYWMN |
| | | CDR2 | 13 | QIRLQRDNYATRYAASVKG |
| | | CDR3 | 3 | GTTY |
| | V$_H$ Domain | | 23 | EVQLVESGGGLVQPGGSLRLSCAASGFTFS<u>NYWMN</u>WIRQAPG KGLEWVG<u>QIRLQRDNYATRYAA</u>SVKGRFTISRDDSKNSVYLQ MNSLKTEDTAVYYCTG<u>GTTY</u>WGQGTLVTVSS |
| | V$_L$ | CDR1 | 11 | KASQNVGTKVA |
| | | CDR2 | 5 | SASIRYT |
| | | CDR3 | 6 | QQFSSYPYT |
| | V$_L$ Domain | | 20 | DIQMTQSPSFLSASVGDRVTITC<u>KASQNVGTKVA</u>WYQQKPGK APKLLIY<u>SASIRYT</u>GVPSRFSGSGSGTEFTLTISSMQPEDFA TYYC<u>QQFSSYPYT</u>FGQGTKLEIK |
| PT1B782 | V$_H$ | CDR1 | 7 | NYWMN |
| | | CDR2 | 14 | QIRLQYDNYATRYAASVKG |
| | | CDR3 | 3 | GTTY |
| | V$_H$ Domain | | 24 | EVQLVESGGGLVQPGGSLRLSCAASGFTFS<u>NYWMN</u>WIRQAPG KGLEWVG<u>QIRLQYDNYATRYAA</u>SVKGRFTISRDDSKNSVYLQ MNSLKTEDTAVYYCTG<u>GTTY</u>WGQGTLVTVSS |
| | V$_L$ | CDR1 | 11 | KASQNVGTKVA |
| | | CDR2 | 5 | SASIRYT |
| | | CDR3 | 6 | QQFSSYPYT |
| | V$_L$ Domain | | 25 | DIQLTQSPSFLSASVGDRVTITC<u>KASQNVGTKVA</u>WYQQKPGK APKLLIY<u>SASIRYT</u>GVPSRFSGSGSGTEFTLTISSMQPEDFA TYYC<u>QQFSSYPYT</u>FGQGTKLEIK |

In one embodiment, a monoclonal antibody or an antigen-binding fragment thereof of the invention has a heavy chain comprising an HCDR1 of SEQ ID NO:1 or 7; an HCDR2 of SEQ ID NO:2, 8, 10, 12, 13 or 14; and an HCDR3 of SEQ ID NO:3. In another embodiment, a monoclonal antibody of the invention has a light chain comprising an LCDR1 of SEQ ID NO:4, 9 or 11; an LCDR2 of SEQ ID NO:5; and an LCDR3 of SEQ ID NO:6.

In preferred embodiments, a monoclonal antibody or an antigen-binding fragment thereof of the invention comprises:

an HCDR1 of SEQ ID NO:1; an HCDR2 of SEQ ID NO:2 and an HCDR3 of SEQ ID NO:3 and an LCDR1 of SEQ ID NO:4; an LCDR2 of SEQ ID NO:5; and an LCDR3 of SEQ ID NO:6;

an HCDR1 of SEQ ID NO:7; an HCDR2 of SEQ ID NO:8 and an HCDR3 of SEQ ID NO:3 and an LCDR1 of SEQ ID NO:9; an LCDR2 of SEQ ID NO:5; and an LCDR3 of SEQ ID NO:6;

an HCDR1 of SEQ ID NO:7; an HCDR2 of SEQ ID NO:10 and an HCDR3 of SEQ ID NO:3 and an LCDR1 of SEQ ID NO:11; an LCDR2 of SEQ ID NO:5; and an LCDR3 of SEQ ID NO:6;

an HCDR1 of SEQ ID NO:7; an HCDR2 of SEQ ID NO:12 and an HCDR3 of SEQ ID NO:3 and an LCDR1 of SEQ ID NO:11; an LCDR2 of SEQ ID NO:5; and an LCDR3 of SEQ ID NO:6;

an HCDR1 of SEQ ID NO:7; an HCDR2 of SEQ ID NO:13 and an HCDR3 of SEQ ID NO:3 and an LCDR1 of SEQ ID NO:11; an LCDR2 of SEQ ID NO:5; and an LCDR3 of SEQ ID NO:6; or an HCDR1 of SEQ ID NO:7; an HCDR2 of SEQ ID NO:14 and an HCDR3 of SEQ ID NO:3 and an LCDR1 of SEQ ID NO:11; an LCDR2 of SEQ ID NO:5; and an LCDR3 of SEQ ID NO:6.

In other embodiments, a monoclonal antibody of the invention that binds PHF-tau comprises one or more CDRs that are at least 97% identical, at least 98% identical or at least 99% identical to a CDR of any of SEQ ID NOs:1, 2, 3, 4, 5, 6, 7, 8, 9, 10, 11, 12, 13 and 14.

In another embodiment, a monoclonal antibody or an antigen-binding fragment thereof of the invention comprises a heavy chain variable region comprising any of SEQ ID NOs:15, 17, 19, 21, 23 and 24 and a light chain variable region comprising any of SEQ ID NOs: 16, 18, 20, 22 and 25.

In another embodiment, a monoclonal antibody or an antigen-binding fragment thereof of the invention comprises:

a heavy chain variable region comprising SEQ ID NO:15 and a light chain variable region comprising SEQ ID NO: 16;

a heavy chain variable region comprising SEQ ID NO:17 and a light chain variable region comprising SEQ ID NO: 18;

a heavy chain variable region comprising SEQ ID NO:19 and a light chain variable region comprising SEQ ID NO: 20;

a heavy chain variable region comprising SEQ ID NO:21 and a light chain variable region comprising SEQ ID NO: 22;

a heavy chain variable region comprising SEQ ID NO:23 and a light chain variable region comprising SEQ ID NO: 20; or a heavy chain variable region comprising SEQ ID NO:24 and a light chain variable region comprising SEQ ID NO: 25.

In another embodiment, a monoclonal antibody or an antigen-binding fragment thereof of the invention that binds PHF-tau comprises a heavy chain variable region comprising an amino acid sequence at least 80%, at least 85%, at least 90%, at least 95%, at least 97%, at least 98%, at least 99% or 100% identical to any of SEQ ID NOs:15, 17, 19, 21, 23 and 24 and/or a light chain variable region comprising an amino acid sequence at least 80%, at least 85%, at least 90%, at least 95%, at least 97%, at least 98%, at least 99% or 100% identical to any of SEQ ID NOs: 16, 18, 20, 22 and 25. In a specific embodiment, the CDR regions are as described in Table 1 such that the amino acid changes are in the non-CDR regions of the variable region.

In another embodiment, an isolated antibody or antigen binding fragment thereof of the invention binds to an epitope comprising 119-126 of human tau protein, wherein the numbering of the amino acid is with reference to the amino acid sequence set forth in SEQ ID NO:31.

Although the embodiments illustrated in the Examples comprise pairs of variable regions, one from a heavy and one from a light chain, a skilled artisan will recognize that alternative embodiments can comprise single heavy or light chain variable regions. The single variable region can be used to screen for variable domains capable of forming a two-domain specific antigen-binding fragment capable of, for example, binding to PHF-tau. The screening can be accomplished by phage display screening methods using for example hierarchical dual combinatorial approach disclosed in PCT Publ. No. WO92/01047. In this approach, an individual colony containing either a H or L chain clone is used to infect a complete library of clones encoding the other chain (L or H), and the resulting two-chain specific antigen-binding domain is selected in accordance with phage display techniques as described.

Another embodiment of the invention is an isolated antibody that binds PHF-tau comprising an antigen-binding site having a heavy chain variable region (VH) of any of SEQ ID NOs:15, 17, 19, 21, 23 and 24 and/or a light chain variable region comprising an amino acid sequence of any of SEQ ID NOs: 16, 18, 20, 22 and 25. In one embodiment, an isolated antibody or antigen binding fragment thereof of the invention comprises a VH having an IMGT germline identifier (Barbie and Lefranc, 1998, Exp. Clin. Immunogenet, 15: 171-183) of IGHV6-3*01, and a VL having an IMGT germline identifier of IGKV6-13*01.

In any of the preceding embodiments, the isolated antibody that binds PHF-tau can be humanized.

Antibodies of the present invention can be produced by a variety of techniques, for example by the hybridoma method (Kohler and Milstein Nature 256:495-7, 1975). Chimeric mAbs containing a light chain and heavy chain variable region derived from a donor antibody (typically murine) in association with light and heavy chain constant regions derived from an acceptor antibody (typically another mammalian species such as human) can be prepared by the method disclosed in U.S. Pat. No. 4,816,567. CDR-grafted mAbs having CDRs derived from a non-human donor immunoglobulin (typically murine) and the remaining immunoglobulin-derived parts of the molecule being derived from one or more human immunoglobulins can be prepared by techniques known to those skilled in the art such as that disclosed in U.S. Pat. No. 5,225,539. Fully human mAbs lacking any non-human sequences can be prepared from human immunoglobulin transgenic mice by techniques referenced in (Lonberg, et al. Nature 368:856-9, 1994, Fishwild, et al. Nat Biotechnol 14:845-51, 1996, Mendez, et al. Nat Genet 15:146-56, 1997). Human mAbs can also be prepared and optimized from phage display libraries (Knappik, et al. J Mol Biol 296:57-86, 2000, Krebs, et al. J Immunol Methods 254:67-84, 2001, Shi, et al. J Mol Biol 397:385-96, 2010).

Antibody humanization can be accomplished using well known methods, such as specificity determining residues resurfacing (SDRR) (U.S. Publ. No. 2010/0261620), resurfacing (Padlan et al. Mol. Immunol. 28:489-98, 1991), super humanization (Int. Pat. Publ. No. WO04/006955) and human string content optimization (U.S. Pat. No. 7,657, 380). Human framework sequences useful for grafting/humanization can be selected from relevant databases by those skilled in the art. The selected frameworks can further be modified to preserve or enhance binding affinity by techniques such as those disclosed in Queen et al. (Queen, et al. *Proc Natl Acad Sci USA* 86:10029-33, 1989) or in U.S. Publ. No. 2011/0092372.

Preparation of PHF-tau to be used as an antigen for immunization or isolating antibodies from phage display libraries can be done using any suitable technique. In an exemplary method, PHF-tau is isolated from brains of patients having AD using well know protocols, such as described in Greenberg and Davies (Greenberg and Davies *Proc Natl Acad Sci USA* 87:5827-31, 1990). PHF-tau can be isolated from the postmortem cortex of an Alzheimer patient. The isolated PHF-tau is characterized for its purity and hyperphosphorylation status with antibodies known to react with PHF-tau. In a typical PHF-tau preparation, the hyperphosphorylated bands migrating at about 60, 64, 68 and 72 kDa in western blot (Spillantini and Goedert *Trends Neurosci* 21:428-33, 1998) are detected by an AT8 antibody that specifically binds hyperphosphorylated PHF-tau but not dephoshporylated PHF-tau.

Antibodies of the present invention can have the characteristics of not binding control tau of SEQ ID NO: 31. Such antibodies can be generated using methods described above and testing the antibodies for their lack of binding to control tau in western blots followed by Coomassie stain as described above. Control tau can be recombinantly expressed and purified using standard methods.

An antibody or antigen binding fragment thereof of the invention can further be evaluated for their specificity for example using immunohistochemistry on control and AD brain slices.

The antibodies of the invention can have affinities towards PHF-tau with a dissociation constant ($K_D$) less than or equal to about $10^{-7}$, $10^{-8}$, $10^{-9}$, $10^{-10}$, $10^{-11}$ or $10^{-12}$ M. The affinity of a given molecule for PHF-tau can be determined experimentally using any suitable method. Such methods can utilize Biacore, ProteOn or KinExA instrumentation, ELISA or competitive binding assays known to those skilled in the art.

Another aspect of the invention is an isolated antibody or an antigen binding fragment that competes for PHF-tau binding with a monoclonal antibody comprising an antigen-binding site having a heavy chain variable region of any of SEQ ID NOs:15, 17, 19, 21, 23 and 24 and a light chain variable region comprising an amino acid sequence of any of SEQ ID NOs: 16, 18, 20, 22 and 25.

Another aspect of the invention is an isolated antibody or an antigen binding fragment that competes for PHF-tau binding with a monoclonal antibody comprising an antigen-binding site having a heavy chain variable region of SEQ ID NOs:15 and a light chain variable region comprising an amino acid sequence of SEQ ID NOs: 16; a heavy chain variable region of SEQ ID NOs:17 and a light chain variable region comprising an amino acid sequence of SEQ ID NOs: 18; a heavy chain variable region of SEQ ID NOs:19 and a light chain variable region comprising an amino acid sequence of SEQ ID NOs: 20; a heavy chain variable region of SEQ ID NOs:21 and a light chain variable region comprising an amino acid sequence of SEQ ID NOs: 22; a heavy chain variable region of SEQ ID NOs:23 and a light chain variable region comprising an amino acid sequence of SEQ ID NOs: 20; or a heavy chain variable region of SEQ ID NOs:24 and a light chain variable region comprising an amino acid sequence of SEQ ID NOs:25.

Competition between binding to PHF-tau can be assayed in vitro using well known methods. For example, binding of MSD Sulfo-Tag™ NHS-ester-labeled antibody to PHF-tau in the presence of an unlabeled antibody can be assessed using immunoassay followed by electrochemiluminescence detection.

Several well known methodologies in addition to competitive binding can be employed to determine the binding epitope of the antibodies of the invention. For example, when the structures of both individual components are known, in silico protein-protein docking can be carried out to identify compatible sites of interaction. Hydrogen-deuterium (H/D) exchange can be carried out with the antigen and antibody complex to map regions on the antigen that can be bound by the antibody. Segment and point mutagenesis of the antigen can be used to locate amino acids important for antibody binding. Co-crystal structure of antibody-antigen complex is used to identify residues contributing to the epitope and paratope.

Antibodies of the invention can be monoclonal antibodies of the IgG, IgD, IgA or IgM isotypes. Antibodies of the invention can be bispecific or multispecific. An exemplary bispecific antibody can bind two distinct epitopes on PHF-tau or can bind PHF-tau and amyloid beta (Aβ). Another exemplary bispecific antibody can bind PHF-tau and an endogenous blood-brain barrier transcytosis receptor such as insulin receptor, transferring receptor, insulin-like growth factor-1 receptor, and lipoprotein receptor. An exemplary antibody is of IgG1 type.

Immune effector properties of the antibodies of the invention can be enhanced or silenced through Fc modifications by techniques known to those skilled in the art. For example, Fc effector functions such as C1q binding, complement dependent cytotoxicity (CDC), antibody-dependent cell-mediated cytotoxicity (ADCC), phagocytosis, down regulation of cell surface receptors (e.g., B cell receptor; BCR), etc. can be provided and/or controlled by modifying residues in the Fc responsible for these activities. For example, the Fc region can contain human IgG4 Fc region having substitutions that eliminate effector function. Thus, the isolated antibody further comprises a Fc region having a modified human IgG4 Fc region containing one or more of the following substitutions: substitution of proline for glutamate at residue 233, alanine or valine for phenylalanine at residue 234 and alanine or glutamate for leucine at residue 235 (EU numbering, Kabat, E. A. et al. (1991) Sequences of Proteins of Immunological Interest, 5th Ed. U.S. Dept. of Health and Human Services, Bethesda, Md., NIH Publication no. 91-3242). Removing the N-linked glycosylation site in the IgG4 Fc region by substituting Ala for Asn at residue 297 (EU numbering) is another way to ensure that residual effector activity is eliminated. Pharmacokinetic properties could also be enhanced by mutating residues in the Fc domain that extend antibody half-life (Strohl *Curr Opin Biotechnol* 20:685-91, 2009).

Additionally, antibodies of the invention can be post-translationally modified by processes such as glycosylation, isomerization, deglycosylation or non-naturally occurring covalent modification such as the addition of polyethylene glycol moieties (pegylation) and lipidation. Such modifications can occur in vivo or in vitro. For example, the antibodies of the invention can be conjugated to polyethylene glycol (PEGylated) to improve their pharmacokinetic profiles. Conjugation can be carried out by techniques known to those skilled in the art. Conjugation of therapeutic antibodies with PEG has been shown to enhance pharmacodynamics while not interfering with function (Knight et al. *Platelets* 15:409-18, 2004, Leong, et al. *Cytokine* 16:106-19, 2001, Yang, et al. *Protein Eng* 16:761-70, 2003).

Another embodiment of the invention is an isolated polynucleotide encoding the antibodies of the invention or their complement or fragments thereof. Exemplary isolated polynucleotides are polynucleotides encoding polypeptides comprising an immunoglobulin heavy chain comprising an HCDR1 of SEQ ID NO:1 or 7; an HCDR2 of SEQ ID NO:2, 8, 10, 12, 13 or 14; and an HCDR3 of SEQ ID NO:3 and has a light chain comprising an LCDR1 of SEQ ID NO:4, 9 or 11; an LCDR2 of SEQ ID NO:5; and an LCDR3 of SEQ ID NO:6. Additional exemplary isolated polynucleotides are polynucleotides encoding polypeptides comprising a heavy chain variable region of any of SEQ ID NOs:15, 17, 19, 21, 23 and 24 and a light chain variable region comprising an amino acid sequence of any of SEQ ID NOs: 16, 18, 20, 22 and 25.

Other polynucleotides which, given the degeneracy of the genetic code or codon preferences in a given expression system, encode the antibodies of the invention are also within the scope of the invention. The isolated nucleic acids of the present invention can be made using well known recombinant or synthetic techniques. DNA encoding the monoclonal antibodies is readily isolated and sequenced using methods known in the art. Where a hybridoma is produced, such cells can serve as a source of such DNA. Alternatively, using display techniques wherein the coding sequence and the translation product are linked, such as phage or ribosomal display libraries, the selection of the binder and the nucleic acid is simplified. After phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria.

Another embodiment of the invention is a vector comprising at least one polynucleotide of the invention. Such vectors can be plasmid vectors, viral vectors, transposon based vectors or any other vector suitable for introduction of the polynucleotides of the invention into a given organism or genetic background by any means.

Another embodiment of the invention is a host cell comprising any of the polynucleotides of the invention. Such host cells can be eukaryotic cells, bacterial cells, plant cells or archeal cells. Exemplary eukaryotic cells can be of mammalian, insect, avian or other animal origins Mammalian eukaryotic cells include immortalized cell lines such as hybridomas or myeloma cell lines such as SP2/0 (American Type Culture Collection (ATCC), Manassas, Va., CRL-1581), NSO (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonza Biologics), CHO-K1 (ATCC CRL-61, Invitrogen) or DG44.

Another embodiment of the invention is a method of making an antibody that binds PHF-tau comprising culturing a host cell of the invention and recovering the antibody produced by the host cell. Methods of making antibodies and purifying them are well known in the art.

Methods of Treatment

Anti-PHF-tau antibodies of the invention or antigen-binding fragments thereof, including Fab, (Fab')2, scFv fragments, or antibodies comprising antigen-binding sites of the antibodies of the invention can be used to treat, reduce or prevent symptoms in patients having a neurodegenerative disease that involves pathological aggregation of tau within the brain.

The disease (tauopathy) to be treated by the methods of the invention includes, but is not limited to, one or more selected from the group consisting of Alzheimer's disease (including familial Alzheimer's disease and sporadic Alzheimer's disease), frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Sträussler-Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, postencephalitic parkinsonism, chronic traumatic encephalopathy, and dementia pugulistica (boxing disease).

Preferably, the disease (tauopathy) is Alzheimer's disease (including familial Alzheimer's disease and sporadic Alzheimer's disease), FTDP-17 or progressive supranuclear palsy.

Most preferably, the disease (tauopathy) is Alzheimer's disease (including familial Alzheimer's disease and sporadic Alzheimer's disease).

While not wishing to be bound by any particular theory, the antibodies of the invention or antigen-binding fragments thereof can exert their beneficial effect by reducing pathological tau aggregation (e.g., by preventing aggregation and/or by decreasing aggregation that has already occurred) and hence the amount of PHF-tau in the brain. The antibodies of the invention or antigen-binding fragments thereof can be used to treat an animal patient belonging to any classification. Examples of such animals include mammals such as humans, rodents, dogs, cats and farm animals. For example, the antibodies of the invention or antigen-binding fragments thereof are useful in the preparation of a medicament for treatment of AD wherein the medicament is prepared for administration in dosages defined herein.

Another embodiment of the invention is a method of reducing aggregation of tau in patients in need thereof comprising administering to the patient a therapeutically effective amount of the isolated antibody of the invention or an antigen-binding fragment thereof for a time sufficient to reduce the aggregation of tau.

Another embodiment of the invention is a method of treating or reducing symptoms of a neurodegenerative disease that involves aggregation of tau in a patient comprising administering to the patient a therapeutically effective amount of the isolated antibody of the invention or antigen-binding fragment thereof for a time sufficient to treat or reduce symptoms of the neurodegenerative disease.

In any of the embodiments above, the neurodegenerative disease that involves aggregation of tau is a tauopathy.

As used herein a "tauopathy" encompasses any neurodegenerative disease that involves the pathological aggregation of tau within the brain. In addition to familial and sporadic AD, other exemplary tauopathies are frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Sträussler-Scheinker disease, Hallervorden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, and chronic traumatic encephalopathy, such as dementia pugulistica (boxing disease). (Morris, et al. *Neuron* 70:410-26, 2011).

A tauopathy-related behavioral phenotype includes cognitive impairments, early personality change and disinhibition, apathy, abulia, mutism, apraxia, perseveration, stereotyped movements/behaviors, hyperorality, disorganization, inability to plan or organize sequential tasks, selfishness/callousness, antisocial traits, a lack of empathy, halting, agrammatic speech with frequent paraphasic errors but relatively preserved comprehension, impaired comprehension and word-finding deficits, slowly progressive gait instability, retropulsions, freezing, frequent falls, non-levodopa responsive axial rigidity, supranuclear gaze palsy, square wave jerks, slow vertical saccades, pseudobulbar palsy, limb apraxia, dystonia, cortical sensory loss, and tremor.

Patients amenable to treatment include asymptomatic individuals at risk of AD or other tauopathy, as well as patients presently showing symptoms. Patients amenable to treatment include individuals who have a known genetic risk of AD, such as a family history of AD or presence of genetic risk factors in the genome. Exemplary risk factors are mutations in the amyloid precursor protein (APP), especially at position 717 and positions 670 and 671 (Hardy and Swedish mutations, respectively). Other risk factors are mutations in the presenilin genes, PS1 and PS2, and ApoE4, family history of hypercholesterolemia or atherosclerosis. Individuals presently suffering from AD can be recognized from characteristic dementia by the presence of risk factors described above. In addition, a number of diagnostic tests are available to identify individuals who have AD. These include measurement of cerebrospinal fluid tau and A1342 levels. Elevated tau and decreased A1342 levels signify the presence of AD. Individuals suffering from AD can also be diagnosed by AD and Related Disorders Association criteria.

Administration/Pharmaceutical Compositions

Anti-PHF-tau antibodies of the invention or antigen-binding fragments thereof are suitable both as therapeutic and prophylactic agents for treating or preventing neurodegenerative diseases that involve pathological aggregation of tau, such as AD or other tauopathies. In asymptomatic patients, treatment can begin at any age (e.g., at about 10, 15, 20, 25, 30 years). Usually, however, it is not necessary to begin treatment until a patient reaches about 40, 50, 60, or 70 years. Treatment typically entails multiple dosages over a period of time. Treatment can be monitored by assaying antibody, or activated T-cell or B-cell responses to the therapeutic agent over time. If the response falls, a booster dosage is indicated.

In prophylactic applications, pharmaceutical compositions or medicaments are administered to a patient susceptible to, or otherwise at risk of, AD or other tauopathy in an amount sufficient to eliminate or reduce the risk, lessen the severity, or delay the onset of the disease, including biochemical, histologic and/or behavioral symptoms of the disease, its complications and intermediate pathological phenotypes presented during development of the disease. In therapeutic applications, compositions or medicaments are administered to a patient suspected of, or already suffering from, such a disease in an amount sufficient to reduce, arrest, or delay any of the symptoms of the disease (biochemical, histologic and/or behavioral). Administration of a therapeutic can reduce or eliminate mild cognitive impairment in patients that have not yet developed characteristic pathology of a disorder. An amount adequate to accomplish therapeutic or prophylactic treatment is defined as a therapeutically- or prophylactically-effective dose. In both prophylactic and therapeutic regimes, compositions or medicaments are usually administered in several dosages until a sufficient immune response has been achieved.

Anti-PHF-tau antibodies or fragments thereof of the invention can be administered in combination with other agents that are effective for treatment of related neurodegenerative diseases.

In the methods of the invention, the "therapeutically effective amount" of the antibody in the treatment or ameliorating symptoms of a tauopathy can be determined by standard research techniques. For example, the dosage of the antibody can be determined by administering the agent to relevant animal models well known in the art.

In addition, in vitro assays can optionally be employed to help identify optimal dosage ranges. Selection of a particular effective dose can be determined (e.g., via clinical trials) by those skilled in the art based upon the consideration of several factors. Such factors include the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems.

The mode of administration for therapeutic use of the antibodies of the invention can be any suitable route that delivers the agent to the host. Pharmaceutical compositions of these antibodies are useful for parenteral administration, e.g., intradermal, intramuscular, intraperitoneal, intravenous, subcutaneous, intranasal or intracranial or they can be administered into the cerebrospinal fluid of the brain or spine.

The antibodies of the invention or antigen-binding fragments thereof can be prepared as pharmaceutical compositions containing an effective amount of the antibody or fragment as an active ingredient in a pharmaceutically acceptable carrier. The term "carrier" refers to a diluent, adjuvant, excipient, or vehicle with which the antibody is administered. Such pharmaceutical vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They can be sterilized by conventional, well-known sterilization techniques (e.g., filtration). The compositions can contain pharmaceutically acceptable auxiliary substances as required to approximate physiological conditions such as pH adjusting and buffering agents, stabilizing, thickening, lubricating and coloring agents, etc. The concentration of the antibodies of the invention in such pharmaceutical formulation can vary widely, i.e., from less than about 0.5%, usually at or at least about 1% to as much as 15 or 20% by weight and will be selected primarily based on required dose, fluid volumes, viscosities, etc., according to the particular mode of administration selected.

The treatment can be given in a single dose schedule, or as a multiple dose schedule in which a primary course of treatment can be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

Thus, a pharmaceutical composition of the invention for intramuscular injection could be prepared to contain 1 ml sterile buffered water, and between about 1 ng to about 100 mg, about 50 ng to about 30 mg or about 5 mg to about 25 mg of an antibody of the invention. Similarly, a pharmaceutical composition of the invention for intravenous infusion could be made up to contain about 250 ml of sterile Ringer's solution, and about 1 mg to about 30 mg or about 5 mg to about 25 mg of an antibody of the invention. Actual methods for preparing parenterally administrable compositions are well known and are described in more detail in, for example, "Remington's Pharmaceutical Science", 15th ed., Mack Publishing Company, Easton, Pa.

The antibodies of the invention and fragments thereof can be lyophilized for storage and reconstituted in a suitable carrier prior to use. This technique has been shown to be effective with antibody and other protein preparations and art-known lyophilization and reconstitution techniques can be employed.

Diagnostic Methods and Kits

Antibodies of the invention can be used in methods of diagnosing AD or other tauopathy in a subject. This method involves detecting, in the subject, the presence of PHF-tau using a diagnostic reagent such as an antibody or a fragment thereof of the present invention.

PHF-tau can be detected in a biological sample from a subject (e.g., blood, urine, cerebral spinal fluid) by contacting the biological sample with the diagnostic antibody reagent, and detecting binding of the diagnostic antibody reagent to PHF-tau in the sample from the subject. Assays for carrying out the detection include well known methods such as ELISA, immunohistochemistry, western blot, or in vivo imaging.

Diagnostic antibodies or similar reagents can be administered by intravenous injection into the body of the patient, or directly into the brain by any suitable route that delivers the agent to the host as exemplified above. The dosage of antibody should be within the same ranges as for treatment methods. Typically, the antibody is labeled, although in some methods, the primary antibody with affinity for PHF-tau is unlabelled and a secondary labeling agent is used to bind to the primary antibody. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size, and/or intensity of labeled PHF-tau, tau aggregates, and/or neurofibrillary tangles in a sample from the subject or in the subject, to corresponding baseline values. The baseline values can represent the mean levels in a population of undiseased individuals. Baseline values can also represent previous levels determined in the same subject.

The diagnostic methods described above can also be used to monitor a subject's response to therapy by detecting the presence of PHF-tau in a subject before, during or after the treatment. A decrease in values relative to baseline signals a positive response to treatment. Values can also increase temporarily in biological fluids as pathological tau is being cleared from the brain.

The present invention is further directed to a kit for performing the above described diagnostic and monitoring methods. Typically, such kits contain a diagnostic reagent such as the antibodies of the invention, and optionally a detectable label. The diagnostic antibody itself can contain the detectable label (e.g., fluorescent molecule, biotin, etc.) which is directly detectable or detectable via a secondary reaction (e.g., reaction with streptavidin). Alternatively, a second reagent containing the detectable label can be utilized, where the second reagent has binding specificity for the primary antibody. In a diagnostic kit suitable for measuring PHF-tau in a biological sample, the antibodies of the kit can be supplied prebound to a solid phase, such as to the wells of a microtiter dish.

The contents of all cited references (including literature references, issued patents, published patent applications, and co-pending patent applications) cited throughout this application are hereby expressly incorporated by reference.

Example 1

Purification of Paired Helical Filament-Tau (PHF-Tau)

PHF-tau was partially purified by a modified method of Greenberg and Davies (Greenberg and Davies *Proc Natl Acad Sci USA* 87:5827-31, 1990). Briefly, postmortem tissue from the cortex obtained from a histologically confirmed Alzheimer patient was partially purified. Typically, 5 mg of frontal cortex was homogenized in 10 vol of cold buffer Buffer H (10 mM Tris, 800 mM NaCl, 1 mM EGTA and 10% sucrose/pH 7.4) using a glass/Teflon Potter tissue homogenizer (IKA Works, Inc; Staufen, Germany) at 1000 rpm. The homogenized material was centrifuged at 27000 g for 20 min in a Sorvall rotor SS34. The pellet was discarded and the supernatant was adjusted to a final concentration of 1% (w/v) N-lauroylsarcosine and 1% (v/v) 2-mercaptoethanol and incubated for 2 h at 37° C. Subsequently the supernatant was centrifuged at 108000 g for 35 min at 20° C. in a Beckman 60Ti rotor. The pellet was carefully washed in PBS and suspended in PBS. The supernatant was centrifuged a second time as described and the final pellet was dissolved, aliquoted and frozen at −80° C. The quality of the PHF-tau preparations was evaluated on a 12% SDS-PAGE and western blot with anti-tau antibodies AT8 and HT7 (ThermoScientific, Rockford, Ill.). A good quality PHF-tau preparation is composed of 4 bands having molecular weights of about 60, 64, 66 and 72 kDa on a Western blot detected with an antibody reactive with hyperphosphorylated PHF-tau such as AT8. Two separate PHF-tau preparations with comparable quality and purity were made from the same brain sample. Preparation 1 was used for immunization.

Example 2

Generation of Monoclonal Antibodies Against PHF-Tau

Anti-PHF-tau antibodies were generated using standard hybridoma technology in normal Balb/c mice (Kohler and Milstein *Nature* 256:495-7, 1975). Obtained hybridomas were seeded in 96-well plates and screened after 10 days in a direct ELISA on 25 ng/well coated PHF-tau as described below. Positive cells were tested for cross-reactivity on 10 ng/well coated with control tau (SEQ ID NO: 31) expressed in *E. Coli* BL21 cells and purified by heat treatment and ammonium sulphate precipitation. PT82 was found to bind to both PHF tau and control tau (SEQ ID NO:31).

Positive cells were immediately subcloned and positive clones were frozen in liquid nitrogen. All hybridomas were grown in Dulbecco's modified Eagle's medium supplemented with 10% fetal calf serum (Hyclone, Europe), Hybridoma Fusion Cloning Supplement (2%) (Roche, Brussels, Belgium) 2% HT (Sigma, USA), 1 mM sodium pyruvate, 2 mM L-glutamine and penicillin (100 U/ml) and Streptomycin (50 mg/ml).

Antibody variable regions were cloned from select hybridoma cells onto mouse IgG1/IgG2/K background and expressed and purified using routine methods. Briefly, PT/82 hybridoma cells were lysed in RLT Buffer (Qiagen catalog #79216) and frozen at −70° C. The lysate was thawed at 37° C. and RNA was isolated using RNeasy 96 Kit (Qiagen catalog #74182).

An aliquot of RNA was used to synthesize cDNA using a gene specific reverse primer mix using primers designed to anneal to the constant region for mouse IgG heavy chain, mouse Kappa light chain and mouse Lambda light chain. An aliquot of cDNA was used in PCR reactions with mouse primer sets designed to amplify either IgG heavy chain variable regions, kappa light chain variable regions or lambda light chain variable regions. The forward primers consisted of multiple primers designed to anneal to Framework 1 and the reverse primer was designed to anneal to the constant region. An aliquot of the PCR products was run on a 2% agarose gel and the heavy and kappa PCR products showed a visible band of correct size.

The heavy chain and kappa light chain PCR products were sequenced (Sanger method) using a heavy chain or kappa light chain reverse primer designed to anneal to the respective constant region. The sequences were analyzed and aligned to identify the closest matching mouse germline. The first ten amino acids of the heavy and kappa chain Framework 1 sequence were replaced using the matching germline sequence. The IgG heavy chain and kappa variable region amino acid sequences were codon optimized and synthesized. The codon optimized IgG heavy chain and kappa light chain variable regions were synthesized and cloned the fragments into a mouse IgG2a isotype heavy chain and kappa light chain isotype expression vectors.

Antibody variable regions were cloned from selected hybridoma cells, sequenced using standard methods, and subcloned into expression vectors for mAb and Fab. Mab was produced on a mouse IgG2a/κ background and expressed and purified by affinity chromatography (protein A). Fab was produced as chimeric versions with the mouse variable domains fused to human IgG1/κ constant domains and a His tag at the C-terminus of the heavy chain. Fab was transiently expressed in HEK293F cells and purified by affinity chromatography (HisTrap).

Example 3

Binding Assessment by Surface Plasmon Resonance (SPR)

The interactions with PHF-tau and recombinant tau were assessed by SPR on ProteOn XPR36 (Bio-Rad, Hercules, Calif.) or Biacore T200 (Biacore, Uppsala, Sweden) instruments for PT82 and its Fab fragment with PHF and soluble (2N4R) tau. Table 2 shows representative results of the affinity assessment of PT82 and its Fab with PHF-tau and soluble-tau.

TABLE 2

| SPR affinities for PT82 and its Fabs | | |
|---|---|---|
| mAb/Fab | PHF-tau $K_D$ (pM) | Sol-tau $K_D$ (pM) |
| PT82 mAb | 2853 ± 281 | NT |
| PT82 Fab | 5006 ± 626 | 1841 (1410-2270) |

Figure 1B:
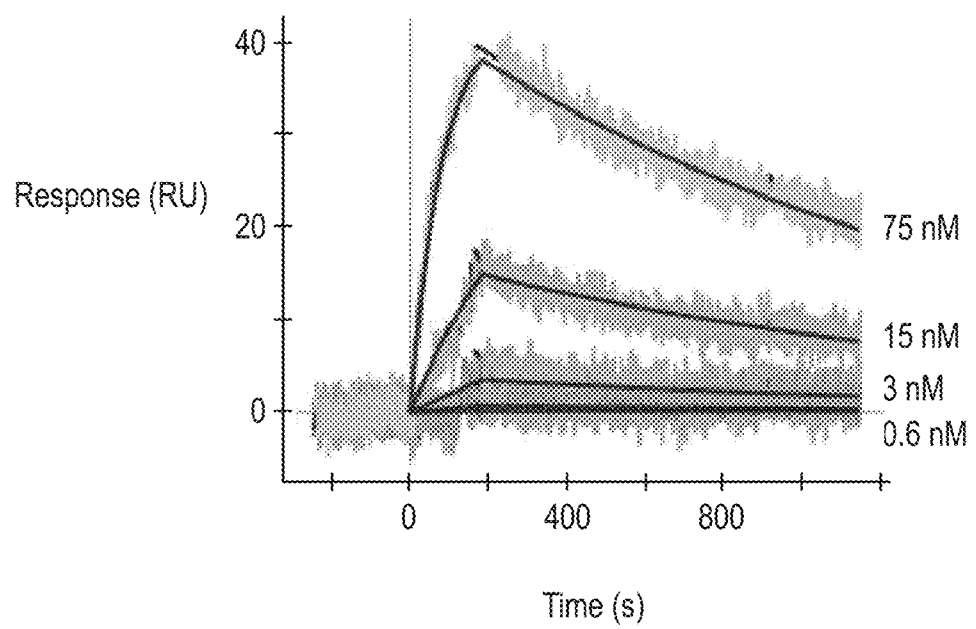
Figure 1C:
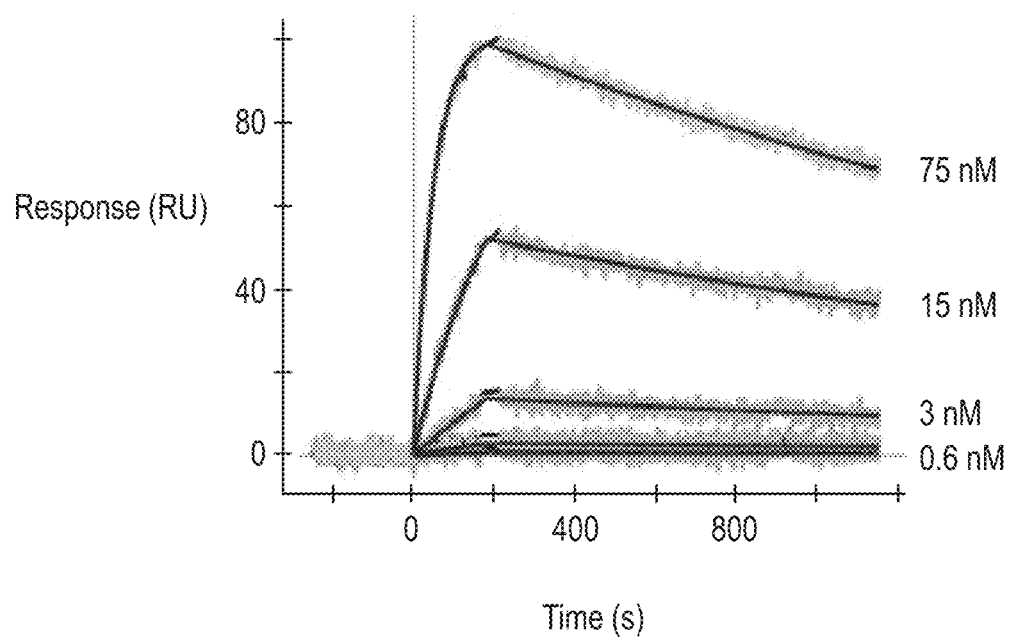

Both PT82 and its Fab bound to PHF-tau. While the Fab fragment of PT82 also bound to soluble Tau (see also FIG. 1). Results from this study demonstrated that PT82 binds PHF-tau and soluble Tau.

Example 4

Direct ELISA for Antibody Selection 25 ng/well PHF-tau was coated overnight at 4° C. in NUNC Maxisorp (Life Technologies) flat-bottom high-binding 96-well micro titer plates in 50 μl/well coating buffer (10 mM Tris, 10 mM NaCl, and 10 mM NaN3, pH 8.5). The next day, the plates were blocked with 75 μl/well of 0.1% casein in PBS for 60 min at room temperature. Next, 50 μl hybridoma supernatant was added and incubated for 1 h at 37° C. After washing, the bound monoclonal antibodies were detected with 50 μl/well of Sheep-anti-mouse IgG conjugated with horseradish peroxidase for 1 hr at 37° C. (Amersham-Pharmacia Biotech). Both reagents were diluted in 0.1% Casein/PBS. The plates were washed and 50 μl of a solution of 0.42 mM 3,5,3',5'-tetramethyl-benzidine, 0.003% (v/v) $H_2O_2$ in 100 mM citric acid and 100 mM disodium hydrogen phosphate (pH 4.3) was added as the substrate. The reaction could proceed for maximum 15 min on a plate shaker at room temperature, after which the color development was stopped with 2 N $H_2SO_4$, 50 μl/well and the plates, were read on a micro titer plate reader at 450 nm (Thermomax, Molecular Devices).

Example 5

Figure 2:
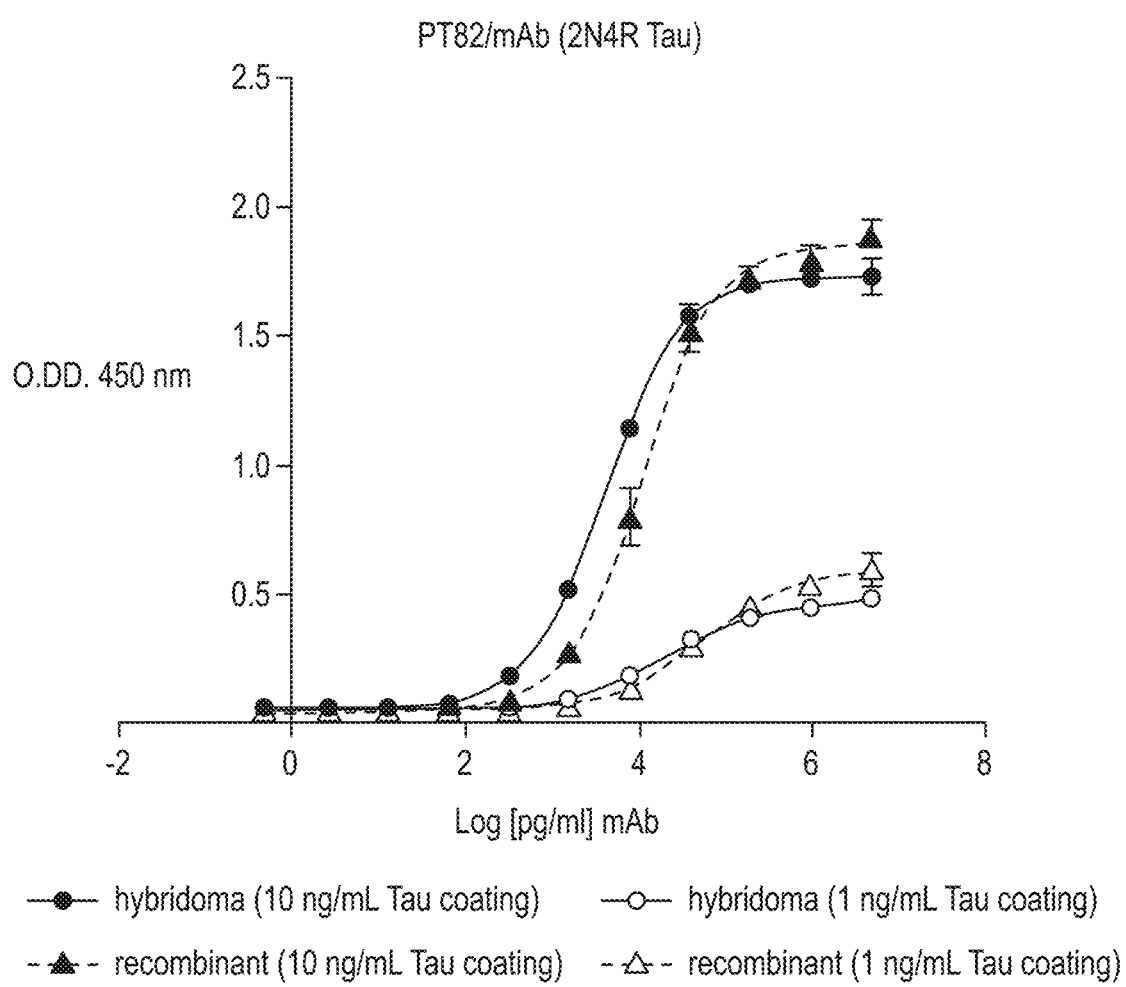
FIG. 2 shows binding of PT82 from hybridoma supernatant and recombinantly expressed PT82 to recombinant 2N4R Tau analyzed by ELISA using two coating concentrations of 2N4R Tau at 10 ng/mL or 1 ng/mL.

Binding to recombinant WT (2N4R; SEQ ID NO:31) tau was analyzed by ELISA where full-length Tau protein (1 ng/mL or 10 ng/mL) was directly coated to the plate and incubated with different concentrations of either recombinantly- or hybridoma produced PT82 antibody (FIG. 2). After incubation with antibodies, plates were again washed and 50 μL per well of HRPO labelled anti-mouse antibody (GE Healthcare) (diluted 1:10000 in blocking buffer) was added. After another washing step detection was performed with "One step" TMB (Thermo Scientific) according to the manufacturers' instructions. Plates were analysed in EnVision® 2102 Multilabel Reader (Perkin Elmer, Waltham, Mass., USA). Binding curves were generated using GraphPad Prism7.0 software. As expected, lower coating concentrations of Tau resulted in lower maximal values (e.g. compare red to green curves where binding of recombinant antibodies to respectively 1 ng/mL or 10 ng/ml are shown). No substantial difference has been observed between binding profiles of recombinant and hybridoma produced antibodies.

Example 6

Spinal Cord Co-Incubation Assay (FRET Assay)

Figure 3A:
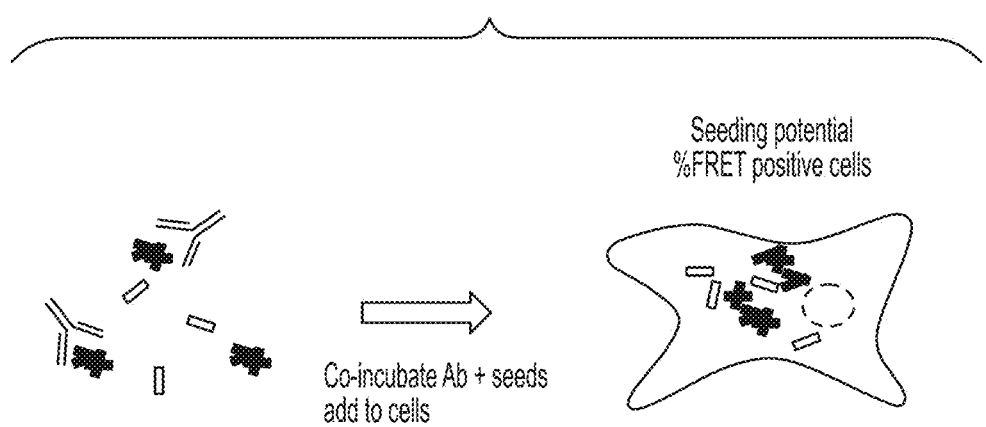
FIGS. 3A-3B show the ability of PT82 mAb to block tau aggregate formation in a FRET assay. (A) shows a diagram of the FRET assay in a cellular model used. (B) shows the efficacy of PT82 in the FRET assay as compared to a negative control mAb (CNT01037/C18A antibody).

Homogenates containing tau seeds for co-incubation were derived from spinal cord tissue from 22- to 23-week-old P301S transgenic animals that contain aggregated transgenic human tau (FIG. 3A). The recipient cells used in the assay were HEK cells stably expressing K18/P301L-YFP and K18/P301L-CFP (Holmes et al., Proc Natl Acad Sci USA. 111(41):E4376-85, 2014). Homogenates containing tau seeds were co-incubated with negative control or PT82 antibody and this mixture was added to receiving chromophore-K18-containing HEK cells for 72 h. K18 aggregate formation was measured by counting FRET-positive cells by FACS.

Figure 3B:
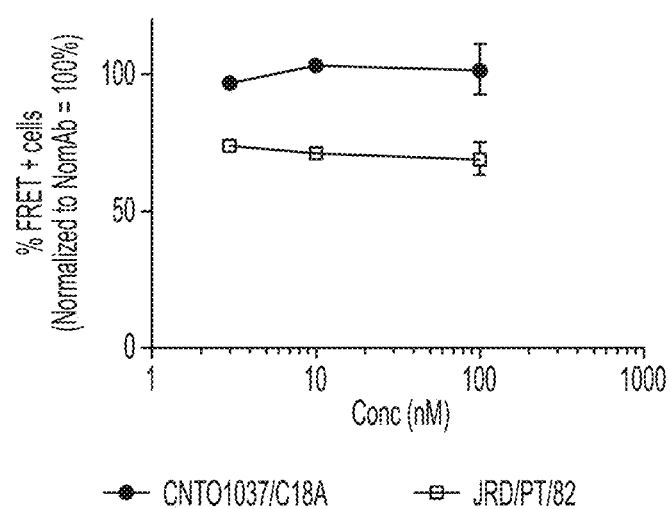

PT82 blocked Tau aggregate induction at a concentration as low as 3 nM (FIG. 3B).

Example 7

Immunodepletion Cellular Assays

Figure 4A:
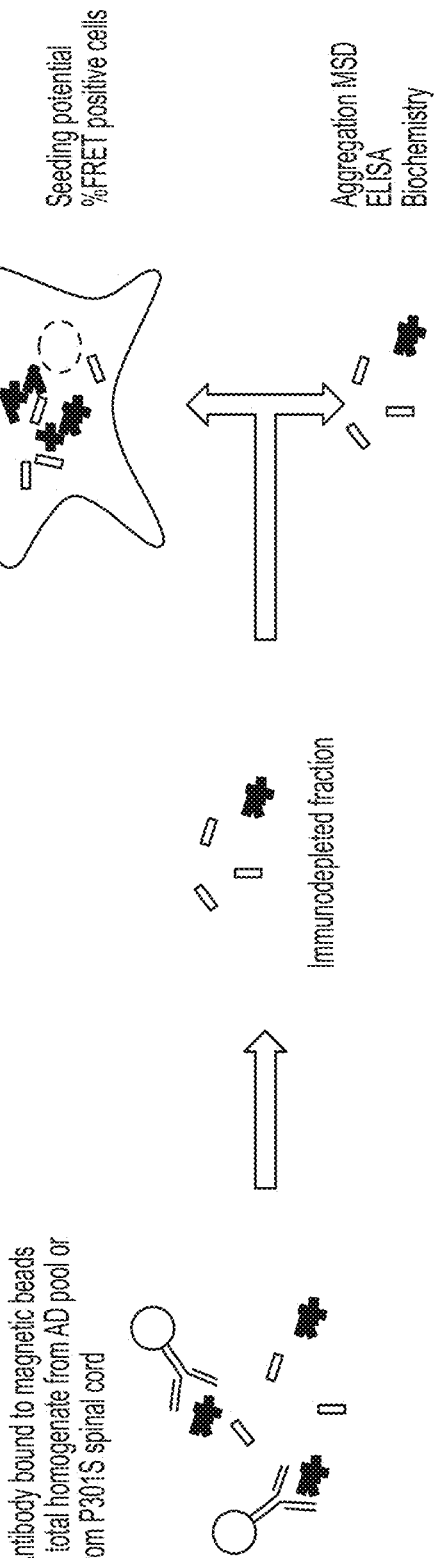
FIGS. 4A-4C show the ability of PT82 mAb to block tau aggregate formation in a immunodepletion assay. (A) shows a diagram of the immunodepletion assay used where PT82 mAb was used to immunodeplete either homogenates from human AD brain or P301S mouse spinal cord extract. PT82 mAb could decrease tau seeds in both AD brain and P301S spinal cord extract as assayed by (B) FRET assay and (C) a Tau aggregation-selective MSD assay.

To investigate if the maximum percentage inhibition value is related to the density of epitopes on the seeds or to the number of seeds that contain the PT82 epitope, immunodepletion assays were performed (FIG. 4A). In the immunodepletion assays, the tau seeds were incubated with negative control or PT82 antibody and removed from the solution with protein G beads. The depleted supernatant was tested for residual seeding capacity in the chromophore-K18-containing HEK cells and analyzed by FACS as previously described (Holmes et al., Proc Natl Acad Sci USA. 111(41): E4376-85, 2014), or for levels of aggregated tau using an aggregation selective Tau assay.

Homogenates containing tau seeds for immunodepletion were generated from spinal cords from 22- to 23-weeks-old P301S transgenic animals or from cryopreserved human AD brain tissue. In the human AD brain immunodepletion assay, the supernatant after depletion was tested in the presence of the transfection reagent Lipofectamine2000 to obtain an acceptable assay window.

Figure 4C:
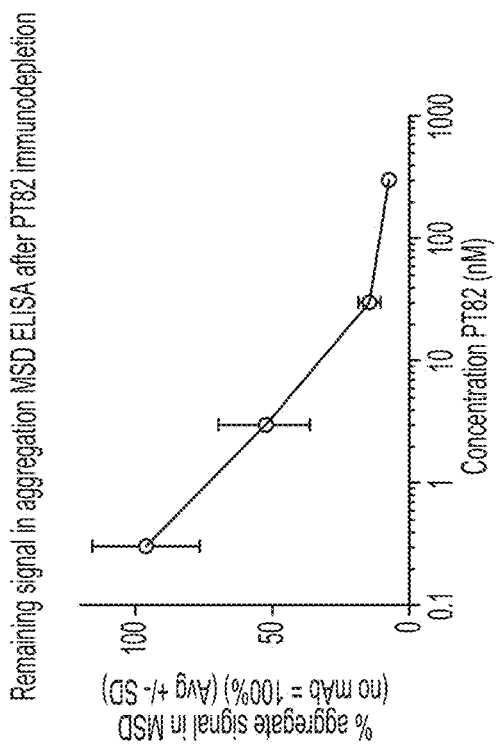
Figure 4B:
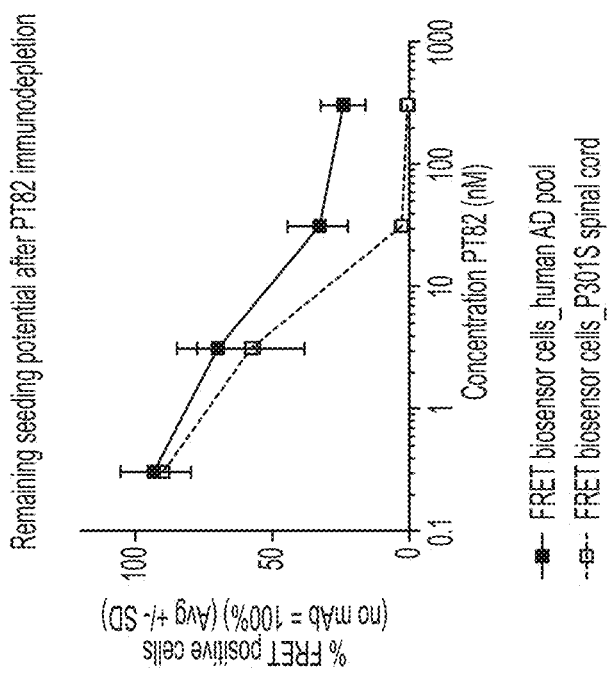

The tau seeding potential (measured in the FRET assay; FIG. 4B) and tau aggregation levels (measured by an aggregated-tau selective MSD assay; FIG. 4C) could be depleted with PT82 in the spinal cord extracts and total homogenates from human AD brain. PT82 inhibited tau seeds derived from both human AD brain and TgP301S spinal cord lysates. The tau seeding could be almost completely depleted with PT82 in the spinal cord extracts.

Example 8

In Vivo Efficacy of Murine PT82 in the ePHF Injection Model

A transgenic P301L mouse injection model has been established, wherein a pro-aggregating fragment of tau, such as synthetic K18 fibrils (Li and Lee, Biochemistry. 45(51): 15692-701, 2006) or PFH-tau seeds derived from human AD brain, is injected in cortical or hippocampal regions of P301L transgenic mouse models at an age at which cell-autonomous aggregation has not started. The injection model aims to mimic the critical extracellular seeding component of tau spreading. The injected K18 or PHF-tau seed induces tauopathy at the injection site and, to a lesser degree, at the connected contralateral region (Peeraer et al., Neurobiol Dis. 73:83-95, 2015). The model enables testing of the anti-seeding potential of antibodies, such as anti-tau antibodies of the invention, when co-injected with the AD-brain-derived PHF-tau seeds or the K18 fibrils (Iba et al., 2015, J Neurosci. 33(3):1024-37, 2013; Iba et al., Acta Neuropathol. 130(3):349-62). Cortical injection of a sarcosyl-insoluble fraction of post-mortem AD brain triggers a slowly progressing increase of tau aggregation. In the injected hemisphere, the first signals are measured 1 month after injection and progress further 3 months after injection. Five months after injection, some animals start to form tangles driven by the P301L mutation (Terwel et al., 2005, Id.). AT8 staining levels increase between 1 and 3 months (ref to PT3 patent), so antibody efficacy experiments are analyzed 2 months after co-injection. Additionally, hippocampal injection of a sarcosyl-insoluble fraction of post-mortem AD brain triggers a dose-dependent progressing increase of tau aggregation measured by MesoScale Discoveries (MSD) analysis of sarcosyl insoluble fractions from the injected hemispheres.

Animal Treatment and Intracranial Injections

For injection studies, transgenic tau-P301L mice, expressing the longest human tau isoform with the P301L mutation (tau-4R/2N-P301L) (Terwel et al., 2005, Id.) were used for surgery at the age of 3 months. All experiments were performed in compliance with protocols approved by the local ethical committee. For stereotactic surgery, the mice received a unilateral (right hemisphere) injection in the hippocampus (AP−2.0, ML+2.0 (from bregma), DV 1.8 mm (from dura)) 3 µl (speed 0.25 µl/min) with a sarcosyl insoluble prep from postmortem AD tissue (enriched paired helical filaments, ePHF) in the presence or absence of monoclonal antibodies. Mice were sacrificed for dissection (2 months after intracranial injection).

Extraction Procedure

Mouse tissue from the injected hemisphere was weighed and homogenized in 6 volumes of homogenization buffer (10 mM Tris HCl (pH7.6); 0.8 M NaCl; 10% w/v sucrose; 1 mM EGTA; PhosStop phosphatase inhibitor cocktail; complete EDTA-free mini protease inhibitors). The homogenate was centrifuged at 28 000×g for 20 minutes, and after taking an aliquot from the resulting supernatant (total homogenate), 1% N-lauroylsarcosine was added. After 90 minutes (900 rpm, 37° C.), the solutions were again centrifuged at 184 000×g for 1 hour. The supernatants were kept as sarcosyl-soluble fraction, whereas the pellet containing the sarcosyl-insoluble material was resuspended in homogenization buffer.

Biochemical Analysis

Coating antibody (AT8) was diluted in PBS (1 µg/ml) and aliquoted into MSD plates (30 uL per well) (L15XA, Mesoscale Discoveries), which were incubated overnight at 4° C. After washing with 5×200 µl of PBS/0.5% Tween-20, the plates were blocked with 0.1% casein in PBS and washed again with 5×200 µl of PBS/0.5% Tween-20. After adding samples and standards (both diluted in 0.1% casein in PBS), the plates were incubated overnight at 4° C. Subsequently, the plates were washed with 5×200 µl of PBS/0.5% Tween-20, and SULFO-TAG™ conjugated detection antibody (AT8) in 0.1% casein in PBS was added and incubated for 2 hr at room temperature while shaking at 600 rpm. After a final wash (5×200 µl of PBS/0.5% Tween-20), 150 µl of 2×buffer T was added, and plates were read with an MSD imager. Raw signals were normalized against a standard curve consisting of 16 dilutions of a sarcosyl insoluble prep from postmortem AD brain (ePHF) and were expressed as arbitrary units (AU) ePHF. Statistical analysis (ANOVA with Bonferroni post test) was performed with the GraphPad prism software and with an 'in house' developed application for automated analysis.

Results

Figure 5B:
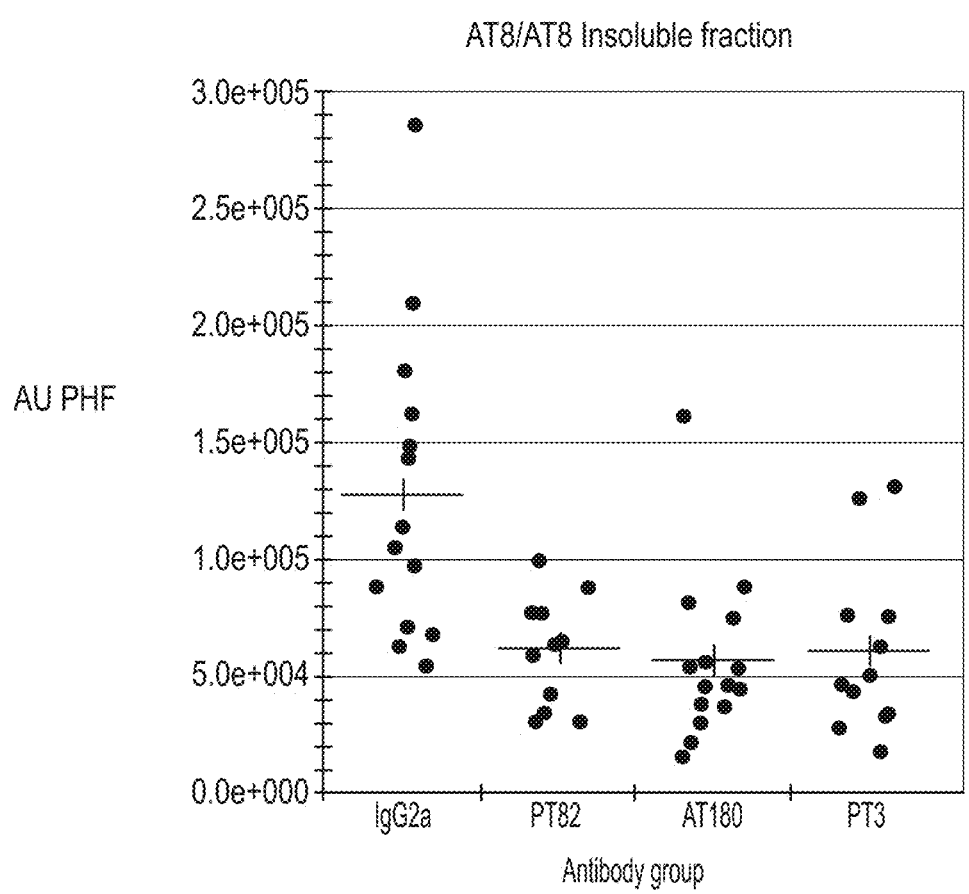

Activity of mouse PT82 (recombinantly expressed as IgG2a) under the hippocampal co-injection model was compared to activity of AT180 and PT3 in one study (FIG. 5, Table 3). Antibodies (4.5 pmole) were co-injected with ePHF tau (0.6 pmoles) into the cortex. Fifteen animals were used in each group. Co-injection of PT82 according attenuated ePHF-induced tau aggregation in P301L mice (FIGS. 5A and 5B). The effect was observed in total homogenates (FIG. 5A) and sarcosyl insoluble homogenates (FIG. 5B).

TABLE 3

Summary of results from functional testing in the injection model

|  |  | AT180 | PT3 | PT82 |
| --- | --- | --- | --- | --- |
| total homogenate | % inhibition | 63.796076 | 54.4989249 | 49.85795 |
|  | P-value | 0.000145 | 0.000806 | 0.001078 |
| insoluble fraction | % inhibition | 55.915265 | 52.9579764 | 51.86379 |
|  | P-value* | <0.0001 | <0.0001 | <0.0001 |

*Statistical analysis was performed by One-Way ANOVA using Bonferroni correction for multiple comparisons.

Figure 6A:
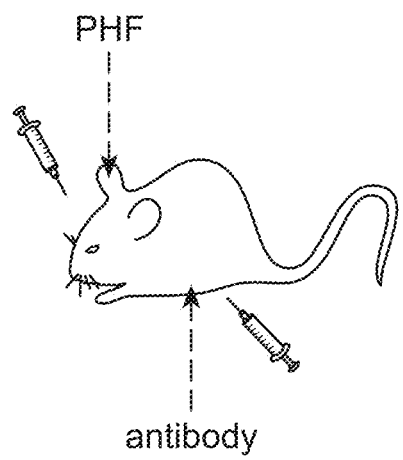
FIGS. 6A-6D show efficacy of PT82 and PT3 upon (A) peripheral dosing (IP injections) of the antibody compared to (B) co-injection of the antibody and PHF intracranially. Efficacy was analyzed in (C) total homogenates and (D) insoluble fractions.
Figure 6B:
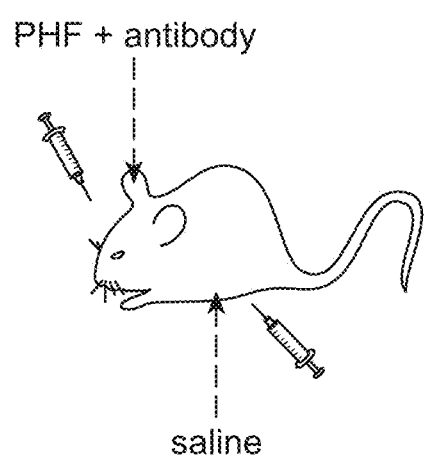
Figure 6C:
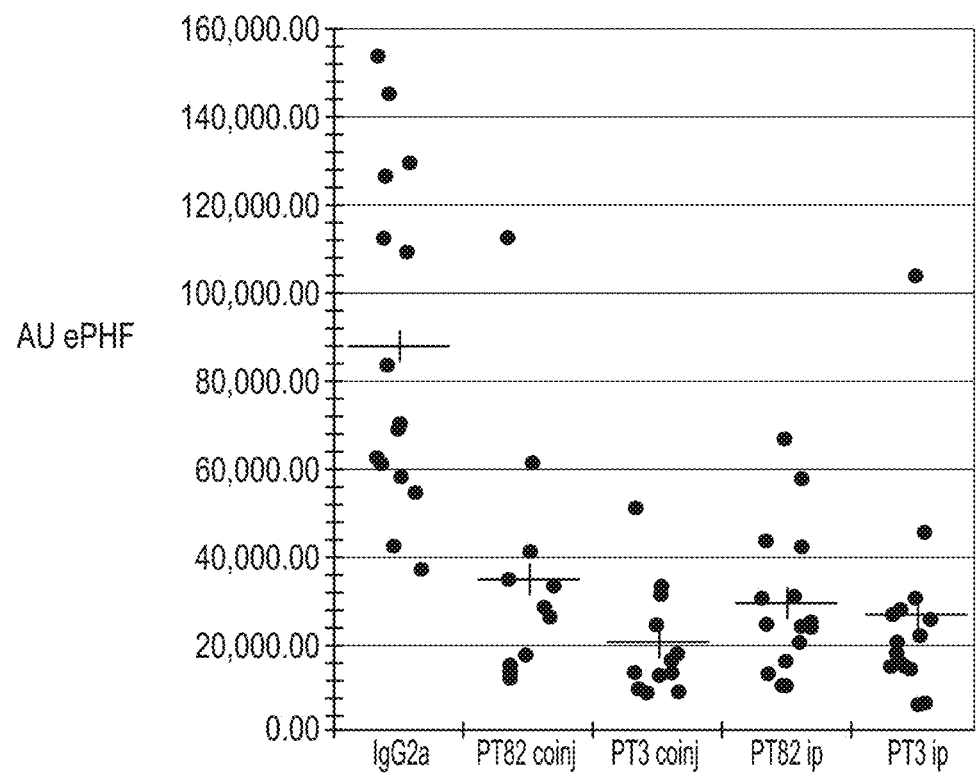
Figure 6D:
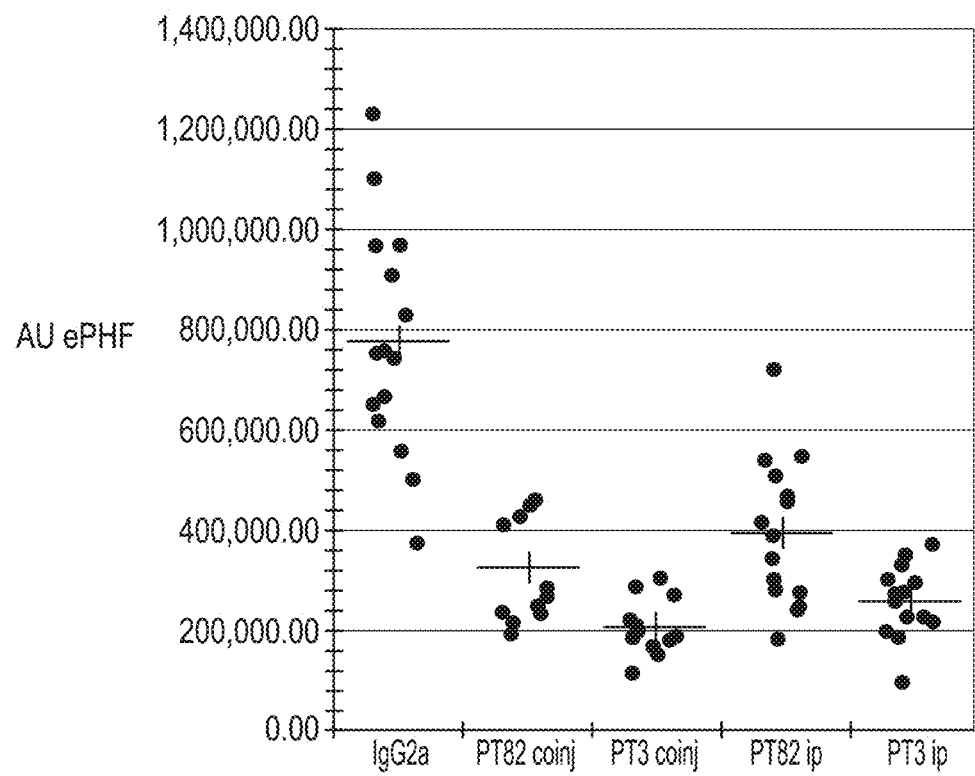

In a follow-up study, efficacy by PT3 and PT82 was compared upon peripheral dosing (20 mg/kg; 2×/week) of the antibody after intracranial injection of PHF (FIG. 6A) and intracranial co-injections (FIG. 6B) of antibody+PHF. The peripheral dosing started 2 weeks before intracranial injections of PHF and continued during the life phase of the experiment. Table 4 shows the amounts of antibody used in the experiments. Consistent with the first study, both co-administration of PT3 and PT82 reduced the ePHF-induced aggregation signal in sarcosyl insoluble fractions (FIG. 6C and Table 5) and in total brain homogenates (FIG. 6D and Table 5). In addition to that, peripheral dosing of the antibodies significantly inhibited the seeding induced by ePHF.

TABLE 4

Amounts of Reagents Used

| Group | Amount ePHF (pmole) | Amount Ab for co-injection (pmole) | Dose Ab for peripheral injection (mg/kg) | n |
| --- | --- | --- | --- | --- |
| IgG-G2a | 0.4 | 3 | 20 | 15 |
| PT3 | 0.4 | 3 | — | 12 |
| PT3 | 0.4 | — | 20 | 14 |
| PT82 | 0.4 | 3 | — | 12 |
| PT82 | 0.4 | — | 20 | 15 |

TABLE 5

Summary of results from functional testing in the injection model

|  |  | PT3 co-inj | PT3 IP | PT82 co-inj | PT82 IP |
| --- | --- | --- | --- | --- | --- |
| total homogenate | % inhibition | 73.34 | 66.68 | 58.23 | 49.10 |
|  | P-value* | <0.0001 | <0.0001 | <0.0001 | <0.0001 |
| insoluble fraction | % inhibition | 77.07 | 69.36 | 60.64 | 66.53 |
|  | P-value* | <0.0001 | <0.0001 | <0.0001 | <0.0001 |

*Statistical analysis was performed by One-Way ANOVA using Bonferroni correction for multiple comparisons.

Example 9

Synthesis of Array Peptides

To reconstruct epitopes of the target molecule a library of peptides (20-mers with an overlap of 18 amino acids) covering the Tau 441 sequence was synthesized. An amino functionalized polypropylene support was obtained by grafting with a proprietary hydrophilic polymer formulation, followed by reaction with t-butyloxy carbonyl-hexamethylenediamine (BocHMDA) using dicyclohexylcarbodiimide (DCC) with N-hydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer). Synthesis of structural mimics was done using Pepscan's proprietary Chemically Linked Peptides on Scaffolds (CLIPS) technology (Timmerman P, Puijk W C, Meloen R H (2007) Functional reconstruction and synthetic mimicry of a conformational epitope using CLIPS technology. J Mol Recognit 20: 283-299. 10.1002/jmr.846 [doi]). CLIPS technology allows to structure peptides into single loops, double loops, triple loops, sheet-like folds, helix-like folds and combinations thereof. CLIPS templates are coupled to cysteine residues. The side-chains of multiple cysteines in the peptides are coupled to one or two CLIPS templates. For example, a 0.5 mM solution of the P2 CLIPS (2,6-bis(bromomethyl)pyridine) is dissolved in ammonium bicarbonate (20 mM, pH 7.8)/acetonitrile (1:3(v/v)). This solution is added onto the peptide arrays. The CLIPS template will bind to side-chains of two cysteines as present in the solid-phase bound peptides of the peptide-arrays (455 wells plate with 3 µl wells). The peptide arrays are gently shaken in the solution for 30 to 60 minutes while completely covered in solution. Finally, the peptide arrays are washed extensively with excess of $H_2O$ and sonicated in disrupt-buffer containing 1% SDS/0.1% beta-mercaptoethanol in PBS (pH 7.2) at 70° C. for 30 minutes, followed by sonication in $H_2O$ for another 45 minutes. The T3 CLIPS carrying peptides were made in a similar way but now with three cysteines.

ELISA Screening

The binding of antibodies (recombinantly expressed as IgG2a) to each of the synthesized peptides was tested in a pepscan-based ELISA. The peptide arrays were incubated with primary antibody solution (overnight at 4° C.). After washing, the peptide arrays were incubated with a 1/1000 dilution of an appropriate antibody peroxidase conjugate (SBA) for one hour at 25° C. After washing, the peroxidase substrate 2,2'-azino-di-3-ethylbenzthiazoline sulfonate (ABTS) and 20 µl/ml of 3 percent H2O2 were added. After one hour, the color development was measured. The color development was quantified with a charge coupled device (CCD)—camera and an image processing system.

Results

Data in FIG. 7 show binding of PT82 to a series of peptides (SEQ ID NOs: 33-42) starting from residue 103 until residue 140 in the Tau441 sequence. For these antibodies, no binding to other Tau peptides was observed. Detailed mapping demonstrated that PT82 binds to peptides with a common motif $_{119}AGHVTQ_{124}$ (SEQ ID NO:32).

Example 10

Humanization of PT82

To find the best combination of humanized heavy and light chains, several human V-region sequences were selected for testing. Selection of human germlines and J-regions was based solely on the overall sequence similarity to the mouse antibody in the framework (FR) region. Neither the CDR sequences, nor their length or canonical structures, were considered in this selection.

The CDR definition used in HFA is described in (Fransson J, et al. *J. Mol. Biol.* 2010; 398:214-231) and corresponds to the Martin's definition (Abhinandan K R and Martin A C. *Mol. Immunol.* 2008; 45:3832-3839). The CDRs are defined as the following (using the Chothia numbering scheme [Chothia C, and Lesk A. *J. Mol. Biol.* 1987; 196:901-917]. At framework positions known to be important for VL/VH pairing and CDR conformation, amino acids were varied in a binary residue library to incorporate human to mouse back-mutations to maintain binding affinity of the humanized V-regions. For PT82, CDRs were grafted into the human HV3-72*01a germline gene. The VH: human/mouse binary combinatorial library included positions 37: I, V; 78: V, L; 93: T, A; 94: R, G. For the light chain, CDRs were grafted into the human KV1-9*01a gene with the VL: human/mouse binary combinatorial library at positions 4: L, M and 78: L, M.

Additionally, several positions in VH and VL were randomized in a phage display library to help improve the affinity of the humanized PT82 (Table 6).

TABLE 6

Affinity maturation library positions

| VH position | VL position |
|---|---|
| Y32 | A32 |
| W33 | A34 |
| N35 | Y49 |
| Q50 | Y55 |
| R52 | Q89 |
| L52a | F91 |
| S52c | S92 |
| D53 | S93 |
| A56 | Y94 |
| R58 | Y96 |
| G95 | |
| T96 | |

The humanization/maturation libraries were generated using degenerate oligonucleotides in overlap PCR. The VH or VL library DNA fragments were then cloned into the pCNTO phagemid (Shi et al., J. Mol. Biol. 397:385-396, 2010; Int. Pat. Publ. No. WO2009/085462; U.S. Pat. Publ. No. US2010/0021477; U.S. Pat. Publ. No. US2012/0108795) in combination with the complementarty mouse V-region. Library ligations were purified and transformed into MC1061F' cells. Cells were grown in 2×YT (Carb) until log phase growth ($OD_{600\ nm} \approx 0.6$) was achieved. Helper phage was added and the cultures were incubated at 37° C. for 30 minutes. Kanamycin and IPTG were added to each culture to final concentrations of 35 ug/mL and 1 mM, respectively, and grown overnight at 30° C. shaking. The phage from the bacterial media was precipitated using PEG/NaCl and re-suspended in PBS.

For affinity maturation panning, Bt-Tau peptide was captured on 50 µl of SA-coated magnetic beads. Antigen concentrations were 10 nM for round 1, 0.1 nM for round 2, and 0.1 nM for round 3. Beads were subjected to 6 washes with PBST and one wash with PBS, followed by *E. coli* infection as described above. Following phage display selections, phagemid DNA was isolated from the infected MC1061F' cells and digested with restriction enzymes to remove the sequence encoding pIX and the linearized plasmid DNA was excised and purified from agarose gels. This DNA was then self-ligated with T4 DNA ligase. The ligated DNA was electroporated into MC1061F' cells and plated onto LB (Carb/Glucose) agar plates.

Colonies from this electroporation were picked for the ELISA screen and assessment of Fab expression. Briefly, Maxisorp 96 well plates were coated with soluble Tau protein. Fab colonies were grown in 2×YT media and Fab expression was induced with IPTG. ELISA plates were washed and Fab secreted into the *E. coli* media was added to each ELISA plate. Plates were washed and Anti-Fab'2: HRP (Jackson ImmunoResearch) was added to the ELISA plates. Plates were washed and chemiluminescent detection reagent was added and plates were read on a Perkin Elmer EnVision plate reader for luminescence.

Figure 8:
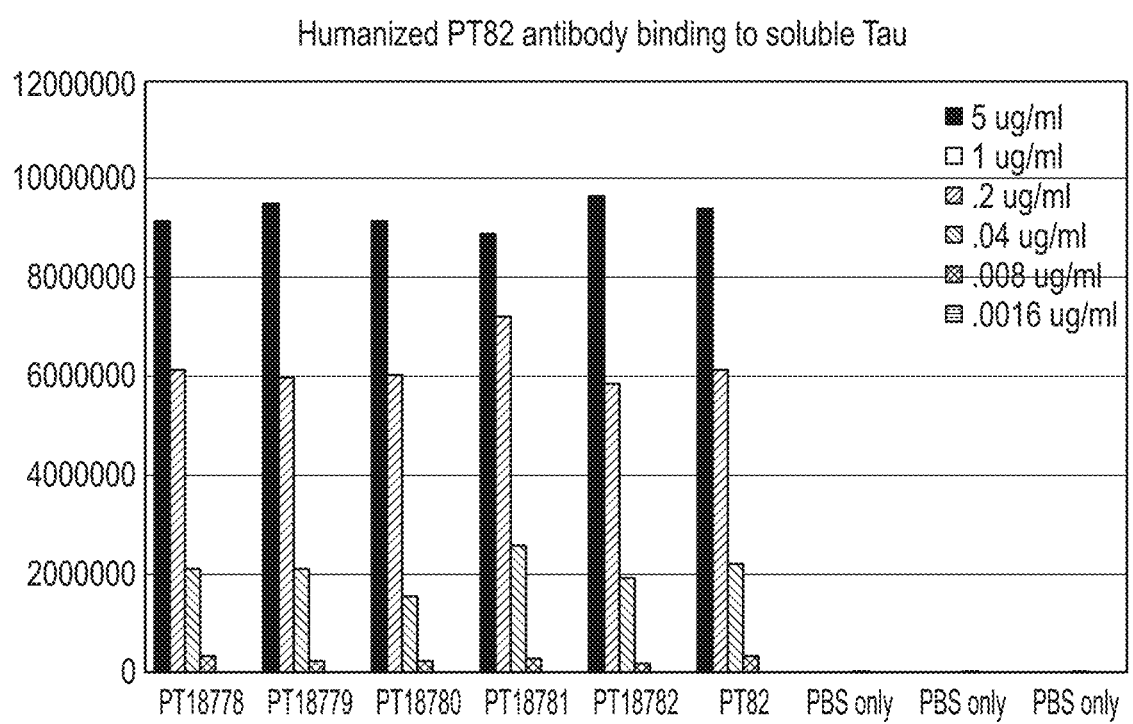
FIG. 8 shows humanized PT82 mAbs binding to soluble tau as measured by ELISA.

Positive clones were sequenced in both VH and VL. VH and VL sequences are listed in Table 1. Unique sequences were cloned into IgG gene expression constructs for expression and purification as full length IgG1 molecules. IgG constructs were transfected into CHO-Expi cells and IgG protein was purified using MabSelectSure resin. Antibodies were then tested in an ELISA for binding to soluble Tau, using anti-human Fc:HRP (Jackson ImmunoResearch), to detect IgG binding. This data is shown in FIG. 8. Humanization did not substantially affect binding to soluble tau as compared to PT82 binding to soluble tau.

The ELISA was done as described for Fabs except that antibodies were tested at five 5-fold dilutions starting at 5 µg/mL in PGS and anti-human Fc:HRP (Jackson ImmunoResearch) was used to detect IgG binding.

While the invention has been described in detail, and with reference to specific embodiments thereof, it will be apparent to one of ordinary skill in the art that various changes and modifications can be made therein without departing from the spirit and scope of the invention.

We claim:

1. An isolated antibody or antigen-binding fragment thereof that binds to paired helical filament-tau (PHF-tau) comprising a heavy chain variable region (VH) comprising a complementary determining region 1 (HCDR1), an HCDR2 and an HCDR3 and a light chain variable region (VL) comprising a complementary determining region 1 (LCDR1), an LCDR2 and an LCDR3, wherein:
   (a) the antibody or antigen-binding fragment thereof comprises an HCDR1 of SEQ ID NO:1; an HCDR2 of SEQ ID NO:2 and an HCDR3 of SEQ ID NO:3 and an LCDR1 of SEQ ID NO:4; an LCDR2 of SEQ ID NO:5; and an LCDR3 of SEQ ID NO:6;
   (b) the antibody or antigen-binding fragment thereof comprises an HCDR1 of SEQ ID NO:7; an HCDR2 of SEQ ID NO:8 and an HCDR3 of SEQ ID NO:3 and an LCDR1 of SEQ ID NO:9; an LCDR2 of SEQ ID NO:5; and an LCDR3 of SEQ ID NO:6;
   (c) the antibody or antigen-binding fragment thereof comprises an HCDR1 of SEQ ID NO:7; an HCDR2 of SEQ ID NO:10 and an HCDR3 of SEQ ID NO:3 and an LCDR1 of SEQ ID NO:11; an LCDR2 of SEQ ID NO:5; and an LCDR3 of SEQ ID NO:6;
   (d) the antibody or antigen-binding fragment thereof comprises an HCDR1 of SEQ ID NO:7; an HCDR2 of SEQ ID NO:12 and an HCDR3 of SEQ ID NO:3 and an LCDR1 of SEQ ID NO:11; an LCDR2 of SEQ ID NO:5; and an LCDR3 of SEQ ID NO:6;
   (e) an HCDR1 of SEQ ID NO:7; an HCDR2 of SEQ ID NO:13 and an HCDR3 of SEQ ID NO:3 and an LCDR1 of SEQ ID NO:11; an LCDR2 of SEQ ID NO:5; and an LCDR3 of SEQ ID NO:6; or
   (f) the antibody or antigen-binding fragment thereof comprises an HCDR1 of SEQ ID NO:7; an HCDR2 of SEQ ID NO:14 and an HCDR3 of SEQ ID NO:3 and an LCDR1 of SEQ ID NO:11; an LCDR2 of SEQ ID NO:5; and an LCDR3 of SEQ ID NO:6.

2. The isolated antibody or antigen-binding fragment of claim 1 comprising:
   (a) a heavy chain variable region comprising a sequence at least 95% identical to SEQ ID NO:15 and a light chain variable region comprising a sequence at least 95% identical to SEQ ID NO:16;
   (b) a heavy chain variable region comprising a sequence at least 95% identical to SEQ ID NO:17 and a light chain variable region comprising a sequence at least 95% identical to SEQ ID NO: 18;
   (c) a heavy chain variable region comprising a sequence at least 95% identical to SEQ ID NO:19 and a light chain variable region comprising a sequence at least 95% identical to SEQ ID NO: 20;

(d) a heavy chain variable region comprising a sequence at least 95% identical to SEQ ID NO:21 and a light chain variable region comprising a sequence at least 95% identical to SEQ ID NO: 22;

(e) a heavy chain variable region comprising a sequence at least 95% identical to SEQ ID NO:23 and a light chain variable region comprising a sequence at least 95% identical to SEQ ID NO: 20; or (f) a heavy chain variable region comprising a sequence at least 95% identical to SEQ ID NO:24 and a light chain variable region comprising a sequence at least 95% identical to SEQ ID NO: 25.

3. The isolated antibody or antigen-binding fragment of claim 1 comprising (a) a heavy chain variable region SEQ ID NO:15 and a light chain variable region comprising SEQ ID NO: 16;

(b) a heavy chain variable region comprising SEQ ID NO:17 and a light chain variable region comprising SEQ ID NO: 18;

(c) a heavy chain variable region comprising SEQ ID NO:19 and a light chain variable region comprising SEQ ID NO: 20;

(d) a heavy chain variable region comprising SEQ ID NO:21 and a light chain variable region comprising SEQ ID NO: 22;

(e) a heavy chain variable region SEQ ID NO:23 and a light chain variable region comprising SEQ ID NO: 20; or (f) a heavy chain variable region comprising SEQ ID NO:24 and a light chain variable region comprising SEQ ID NO: 25.

4. The isolated antibody or antigen-binding fragment of claim 1 that is humanized.

5. An isolated nucleic acid encoding the antibody or antigen-binding fragment of claim 1.

6. A vector comprising the isolated nucleic acid of claim 5.

7. A host cell comprising the nucleic acid of claim 6.

8. A pharmaceutical composition comprising the isolated antibody or antigen-binding fragment of claim 1 and a pharmaceutically acceptable carrier.

9. A pharmaceutical composition comprising the isolated antibody or antigen-binding fragment of claim 4 and a pharmaceutically acceptable carrier.

10. A method of reducing pathological tau aggregation or spreading of tauopathy in a subject in need thereof, comprising administering to the subject the pharmaceutical composition of claim 8.

11. A method of reducing pathological tau aggregation or spreading of tauopathy in a subject in need thereof, comprising administering to the subject the pharmaceutical composition of claim 9.

12. A method of treating a tauopathy in a subject in need thereof, comprising administering to the subject the pharmaceutical composition of claim 8.

13. A method of treating a tauopathy in a subject in need thereof, comprising administering to the subject the pharmaceutical composition of claim 9.

14. A method of treating a tauopathy in a subject in need thereof, comprising administering to the subject the pharmaceutical composition of claim 8, wherein the tauopathy is selected from the group consisting of Alzheimer's disease, frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Straussler-Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, postencephalitic parkinsonism, chronic traumatic encephalopathy, and dementia pugulistica.

15. A method of treating a tauopathy in a subject in need thereof, comprising administering to the subject the pharmaceutical composition of claim 9, wherein the tauopathy is selected from the group consisting of Alzheimer's disease, frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Straussler-Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, postencephalitic parkinsonism, chronic traumatic encephalopathy, and dementia pugulistica.

16. A method of producing the antibody or antigen-binding fragment of claim 1, comprising culturing a cell comprising a nucleic acid encoding the antibody or antigen-binding fragment under conditions to produce the antibody or antigen-binding fragment, and recovering the antibody or antigen-binding fragment from the cell or cell culture.

17. A method of producing a pharmaceutical composition comprising the humanized antibody or antigen-binding fragment of claim 1, comprising combining the antibody or antigen-binding fragment with a pharmaceutically acceptable carrier to obtain the pharmaceutical composition.

18. A method of detecting the presence of PHF-tau in a biological sample from a subject, comprising contacting the biological sample with the antibody or antigen-binding fragment of claim 1, and detecting binding of the antibody or antigen-binding fragment to PHF-tau in the sample from the subject.

19. The method of claim 18, wherein the biological sample is a blood, urine, or cerebral spinal fluid sample.

* * * * *